United States Patent
Su et al.

(10) Patent No.: US 11,630,863 B2
(45) Date of Patent: *Apr. 18, 2023

(54) DATA STORAGE BASED ON ENCODED DNA SEQUENCES

(71) Applicant: Intel Corporation, Santa Clara, CA (US)

(72) Inventors: Xing Su, Menlo Park, CA (US); Kai Wu, Mountain View, CA (US); Noureddine Tayebi, Menlo Park, CA (US); Grace Credo, San Mateo, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/403,791

(22) Filed: Aug. 16, 2021

(65) Prior Publication Data
US 2022/0019621 A1 Jan. 20, 2022

Related U.S. Application Data

(63) Continuation of application No. 15/929,022, filed on Jun. 19, 2018, now Pat. No. 11,093,547.

(51) Int. Cl.
*G06F 16/901* (2019.01)
*H03M 7/30* (2006.01)
(Continued)

(52) U.S. Cl.
CPC ........ *G06F 16/9017* (2019.01); *G06F 16/116* (2019.01); *G06F 16/1794* (2019.01);
(Continued)

(58) Field of Classification Search
CPC ............... G06F 16/9017; G06F 16/116; G06F 16/1794; G16B 30/00; G16B 50/50; H03M 7/30; H03M 7/3088
(Continued)

(56) References Cited

U.S. PATENT DOCUMENTS

| 5,858,705 A | 1/1999 | Wei et al. |
| 6,238,884 B1 | 5/2001 | Short et al. |

(Continued)

OTHER PUBLICATIONS

Yazdi et al.; "A Rewritable, Random-Access DNA-Based Storage System;" Scientific Reports; (Sep. 18, 2015); 10 pages; vol. 5, Issue 14138.
Yazdi et al.; "Portable and Error-Free DNA-Based Data Storage;" Scientific Reports; (Jul. 10, 2017); 6 pages; vol. 7, Issue 5011.
(Continued)

*Primary Examiner* — Jean B Jeanglaude
(74) *Attorney, Agent, or Firm* — Compass IP Law PC

(57) ABSTRACT

Devices, methods, and systems for encoding data as DNA are provided. An encoder device can include circuitry to encode a data file having a bit sequence encoding data and to generate a virtual DNA (VDNA) sequence of virtual nucleotide bases (Vnb) that reversibly encodes the bit sequence of the data file, divide the VDNA sequence into a plurality of VDNA fragments, associate each VDNA fragment with an archive library sequence (Arc_SEQ), and generate a read instruction (READ) sequence of differences between each VDNA fragment and each associated Arc_SEQ including sufficient instruction to facilitate regeneration of each VDNA fragment from each associated Arc_SEQ. A codeword sequence (Code_SEQ) is additionally generated for each VDNA fragment that includes a codename identifying the associated Arc_SEQ, the READ sequence associated with the VDNA fragment, and an index sequence (Idx_SEQ) including an index mapping of the VDNA fragment in the VDNA sequence.

25 Claims, 10 Drawing Sheets

Specification includes a Sequence Listing.

(51) Int. Cl.
  *G06F 16/11* (2019.01)
  *G06F 16/178* (2019.01)
  *G16B 30/00* (2019.01)
  *G16B 50/50* (2019.01)

(52) U.S. Cl.
  CPC ............ *G16B 30/00* (2019.02); *G16B 50/50* (2019.02); *H03M 7/30* (2013.01); *H03M 7/3088* (2013.01)

(58) Field of Classification Search
  USPC ..................................................... 341/50, 51
  See application file for complete search history.

(56) References Cited

U.S. PATENT DOCUMENTS

| | | | |
|---|---|---|---|
| 9,384,320 B2 * | 7/2016 | Church | G06N 3/123 |
| 9,996,778 B2 * | 6/2018 | Church | G06K 19/00 |
| 10,032,000 B1 | 7/2018 | Harris et al. | |
| 10,323,277 B2 | 6/2019 | McKernan et al. | |
| 10,450,562 B2 | 10/2019 | Brown | |
| 10,460,220 B2 * | 10/2019 | Church | G06K 19/022 |
| 10,622,096 B2 | 4/2020 | Rooyen et al. | |
| 10,725,027 B2 | 7/2020 | Bell et al. | |
| 10,818,378 B2 | 10/2020 | Hutchison, III et al. | |
| 10,902,937 B2 | 1/2021 | Sheinin et al. | |
| 10,956,806 B2 * | 3/2021 | Masuda | C07H 21/04 |
| 2008/0015116 A1 | 1/2008 | Bass et al. | |
| 2009/0105959 A1 | 4/2009 | Braverman et al. | |
| 2012/0089608 A1 | 4/2012 | Ganeshalingam et al. | |
| 2017/0247689 A1 | 8/2017 | Brown | |
| 2019/0093102 A1 | 3/2019 | Jung et al. | |

OTHER PUBLICATIONS

Zhang; "Cheap DNA Sequencing is Here. Writing DNA is Next;" Wired.com; (Nov. 20, 2015); 5 pages; [retrieved Mar. 20, 2019]; Retrieved from.
Adjeroh et al.; "DNA Sequence Compression using the Burrows-Wheeler Transform;" In Proceedings IEEE Computer Science Conference on bioinfomnatics; (Aug. 2002); pp. 303-313.
Ailenberg et al.; "An Improved Huffman Coding Method for Archiving Text, Images, and Music Characters in DNA;" Bio Techniques; (Sep. 2009); pp. 747-754; vol. 47, No. 3.
Apostolico et al.; "Off-Line Compression by Greedy Textual Substitution;" In Proceedings of Data Compression Conference; (Nov. 2000); pp. 1173-1744; vol. 88, No. 11.
Arram et al.; "FPGA Acceleration of Reference-Based Compression for Genomic Data;" In: Field Programmable Technology (FPT); 2015 International Conference; (Dec. 7-9, 2015); pp. 9-16.
Bancroft et al.; "Long-Term Storage of Information in DNA;" Science; (Sep. 7, 2001); pp. 1763-1765; vol. 293.
Behzadi et al.; "DNA Compression Challenge Revisited: A Dynamic Progranuning Approach;" In: Combinatorial Pattern Matching (CPM); CPM Annual Symposium; (2005); pp. 190-200; vol. 3537.
Blawat et al.; "Forward Error Correction for DNA Data Storage;" Procedia Computer Science; (2016); pp. 1011-1022; vol. 80.
Bornholt et al.; "A DNA-Based Archival Storage System;" In: ACM Architectural Support for Programming Languages and Operating Systems; 21st International Conference (ASPLOS 2016); pp. 637-649.
Brandon et al.; "Data Structures and Compression Algorithms for Genomic Sequence Data;" Bioinformatics; (May 15, 2009); pp. 1731-1738; vol. 25, No. 14.
Cao et al.; "A Simple Statistical Algorithm for Biological Sequence Compression;" In: Proceedings of Data Compression Conference; (2007); pp. 43-52.
Chen et al.; "DNACompress: Fast and Effective DNA Sequence Compression;" Bioinformatics; (Jun. 17, 2002); pp. 1696-1698; vol. 18, No. 12.

Chern et al.; "Reference Based Genome Compression;" In: Proceedings of IEEE Information Theory Workshop (Apr. 2012); 5 pages; arXiv:1204.1912v1.
Christley et al.; "Human Genomes as Email Attachments;" Bioinformatics; (2009); pp. 274-275; vol. 25, No. 2.
Deorowicz et al.; "Compression of DNA Sequence Reads in FASTQ Format;" Bioinformatics; (Jan. 19, 2011); pp. 860-862; vol. 27, No. 6.
Deorowicz et al.; "GDC 2: Compression of Large Collections of Genomes;" Nature Scientific Reports; (Jun. 25, 2015); 12 pages; vol. 5, No. 11565.
Erlich et al.; "DNA Fountain Enables a Robust and Efficient Storage Architecture;" Science; (Mar. 3, 2017); pp. 950-954; vol. 355.
Fritz et al.; "Efficient Storage of High Throughput DNA Sequencing Data Using Reference-Based Compression;" Genome Research; (2011); pp. 734-740; vol. 21.
Giancarlo et al.; "Textual Data Compression in Computational Biology: A Synopsis;" Bioinformatics; (Feb. 25, 2009); pp. 1575-1586; vol. 25, No. 13.
Goldman et al.; "Toward Practical High-Capacity Low-Maintenance Storage of Digital Information in Synthesized DNA;" Nature; (Jan. 2013); pp. 77-80; vol. 494, No. 7435.
Grass et al.; "Robust Chemical Preservation of Digital Information on DNA in Silica with Error-Correcting Codes;" Angewandte Chemie International Edition; (2015); pp. 2552-2555; vol. 54, No. 8.
Grumbach et al.; "A New Challenge for Compression Algorithms: Genetic Sequences;" Information Processing & Management; (1994); pp. 875-886; vol. 30.
Gusev et al.; "On the Complexity Measures of Genetic Sequences;" Bioinformatics; (Aug. 4, 1999); pp. 994-999; vol. 15, No. 12.
Haiman; "Notes on Reed-Solomon Codes;" (Feb. 2003); 14 pages.
Huffman; "Huffman Coding | Greedy Algo-3;" GeeksforGeeks.org; (Nov. 3, 2012); 15 pages; [ retrieved Mar. 20, 2019]; Retrieved from.
Korodi et al.; "An Efficient Normalized Maximum Likelihood Algorithm for DNA Sequence Compression;" In: ACM Transactions on Information Systems; (Jan. 2005); pp. 3-34; vol. 23, No. I.
Korodi et al.; "Normalized Maximum Likelihood Model of Order-I for the Compression of DNA Sequences;" In: IEEE Data Compression Conference, (DCC 2007); pp. 33-42.
Kreft et al.; "Self-Indexing Based on LZ77;" Combinatorial Pattern Matching; (2011); pp. 41-54; vol. 6661.
Kristi; "Tornado and Luby Transform Codes;" 6.454 Presentation; [slides]; (Oct. 22, 2003); 27 pages.
Kuruppu et al.; "Iterative Dictionary Construction for Compression of Large DNA Data Sets;" In: IEEE/ACM Transactions on Computational Biology and Bioinformatics; (Jan./Feb. 2012); pp. 137-149; vol. 9, No. I.
Kuruppu et al.; "Optimized Relative Lempel-Ziv Compression of Genomes;" In: Proceedings in Research and Practice in Information Technology; 34th Annual Australasian Computer Science Conference; (ACSC 2011); 8 pages.
Li et al.; "DNA-Compact: DNA COMpression Based on a Pattern-Aware Contextual Modeling Technique;" PLoS One; (Nov. 25, 2013); 13 pages; vol. 8, Issue 11 e80377.
Mackay; "Fountain Codes;" Capacity Approaching Codes Design and Implementation Special Section; IEE Proceedings Communication; (Dec. 2005); pp. 1062-1068; vol. 152, No. 6.
Makinen et al.; "Storage and Retrieval of Highly Repetitive Sequence Collections;" Journal of Computational Biology; (2010); pp. 281-308; vol. 17.
Mantaci et al.; "An Extension of the Burrows Wheeler Transform and Applications to Sequence Comparison and Data Compression;" Lecture Notes in Computer Science; In: Combinatorial Pattern Matching; (CPM 2005); pp. 178-189; vol. 3537.
Manzini et al.; "A Simple and Fast DNA Compressor;" Software—Practice and Experience; (Nov. 2004); pp. 1397-1411; vol. 34.
Matsumoto et al.; "Biological Sequence Compression Algorithms; "Genome Informatics; (2000); pp. 43-52; vol. 11.
Notice of Allowance for U.S. Appl. No. 15/929,022, dated Apr. 14, 2021,10 pages.

(56) References Cited

OTHER PUBLICATIONS

Phong; "Finite Context Modelling;" www.hugi.scene.org; (Jan. 2, 2000); 6 pages; [retrieved on Mar. 6, 2019]; Retrieved from.

Pinho et al.; "On the Representability of Complete Genomes by Multiple Competing Finite-Context (Markov) Models;" PLoS ONE; (Jun. 30, 2011); e21588; vol. 6, Issue 6.

Pinho et al.; "GReEn: A Tool for Efficient Compression of Genome Resequencing Data;" Nucleic Acids Research (2012); e27; vol. 40, No. 4.

Portney et al.; "Length-Based Encoding of Binary Data in DNA;" Langmuir; (2008); pp. 1613-1616; vol. 24, No. 5.

Powell et al.; "Discovering Simple DNA Sequences by Compression;" Pacific Symposium on Biocomputing; (1998); pp. 597-608.

Quan et al.; "Parallel On-Chip Gene Synthesis and Application to Optimization of Protein Expression;" Nature Biotechnology; (May 2011); pp. 449-453; vol. 29, No. 5.

Srinivasa et al.; "Efficient Compression of Non-Repetitive Sequences using Dynamic Programming;" In: IEEE Advanced Computing and Communications; 2006 International Conference.

Suyehira et al.; A Coding Scheme for Nucleic Acid Memory (NAM); In: IEEE Workshop on Microelectronics and Electron Devices; 14th Annual Conference; (2017 WMED); (Apr. 21, 2017); 3 pages.

Tabus et al.; "DNA Sequence Compression using the Normalized Maximum Likelihood Model for Discrete Regression;" In: IEEE Proceedings of Data Compression; (DCC 2003); pp. 253-262.

Wang et al.; "A Novel Compression Tool for Efficient Storage of Genome Resequencing Data;" Nucleic Acids Research; (2011); e45; vol. 39, No. 7.

Westall et al.; "An Introduction to Galois Fields and Reed-Solomon Coding;" Clemson University, Clemson, SC; (Oct. 4, 2010); 16 pages.

Wong et al.; "Organic Data Memory Using the DNA Approach;" Communications of the ACM; (Jan. 2003); pp. 95-98; vol. 46, No. I.

Yachie et al.; "Alignment-Based Approach for Durable Data Storage into Living Organisms;" Biotechnology Progress (2007); pp. 501-505; vol. 23.

\* cited by examiner

Data File 01001001 01101110 01110100 01100101 01101100 00100000 01001100 01100001

| VDNA Digit | 1 | 2 | 3 | 4 | 5 | 6 |
|---|---|---|---|---|---|---|
| | x y | x y,y | x y | x y | x y | x y,y |
| Binary Digit | 1 | 2,3 | 4 | 5 | 6,7 | 8 |

FIG. 2B

| VDNA Digit (SEQ ID NO: 04) | 1 | 2 | 3 | 4 | 5 | 6 |
|---|---|---|---|---|---|---|
| | A 0 | G 10 | A 0 | C 1 | A 00 | C 1 |
| Binary Digit | 1 | 2,3 | 4 | 5 | 6,7 | 8 |

| | 1 | 2 | 3 | 4 | 5 | 6 |
|---|---|---|---|---|---|---|
| | A 0 | T 11 | G 0 | T 1 | T 11 | G 0 |
| | 1 | 2,3 | 4 | 5 | 6,7 | 8 |

FIG. 2C

Single-Digit Table

| | Bit Value | Preceding Vnb | |
|---|---|---|---|
| | | G/C | A/T |
| Single Binary Digit | 0 | A | G |
| | 1 | T | C |

Double-Digit Table

| | Double Digit Value | Vnb |
|---|---|---|
| Double Binary Digit | 00 | A |
| | 01 | C |
| | 10 | G |
| | 11 | T |

FIG. 2D

Encoded VDNA Sequence (SEQ ID NO:05)

| AGACAC | ATGTTG | ATCAGA | GTGAGT | GTGTGA | GCAGAG | AGACGA | GTGAAC |
| 01001001 | 01101110 | 01110100 | 01100101 | 01101100 | 00100000 | 01001100 | 01100001 |

| ATGACA | GTCACT | GCAGAG | AGAGCT | AGACGT | GGACAC | AGTGGA |
| 01100010 | 01110011 | 00100000 | 01000011 | 01001101 | 01001001 | 01010100 |

FIG. 2E

DATA STORAGE BASED ON ENCODED DNA SEQUENCES

CROSS-REFERENCE TO RELATED APPLICATIONS

This application is a continuation of U.S. patent application Ser. No. 15/929,022, filed Jun. 19, 2018. The entire specification of which is hereby incorporated herein by reference in its entirety.

BACKGROUND

It is estimated that by the year 2040, the total amount of digital information to be stored will reach about $2.5 \times 10^{25}$ bytes. At current data storage densities, this amount of data would exceed the storage capabilities of datacenters, and the raw material required to generate sufficient storage media would exhaust the available Si supply. This problem would proliferate as data is backed up or archived, which is currently on a typical 10-year cycle for many datacenters. In addition to the lack of sufficient material to create storage media, the energy required to run the needed number of datacenters managing the data is prohibitive.

BRIEF DESCRIPTION OF THE DRAWINGS

FIG. 2A shows an illustration of a binary data file sequence in accordance with an example embodiment;

FIG. 2B shows an illustration of a VDNA digit-to-binary digit correspondence in a single byte-unit for an encoding process in accordance with an example embodiment;

FIG. 2C shows an illustration of the encoding of two byte-units for an encoding process in accordance with an example embodiment;

FIG. 2D shows an illustration of a single-digit table and a double-digit table for encoding a pattern of single binary digits and double binary digits to Vnbs, respectively, in accordance with an example embodiment;

FIG. 2E shows an illustration of the binary data file sequence of FIG. 2A with a corresponding VDNA encoded sequence in accordance with an example embodiment;

DESCRIPTION OF EMBODIMENTS

Figure 1A:
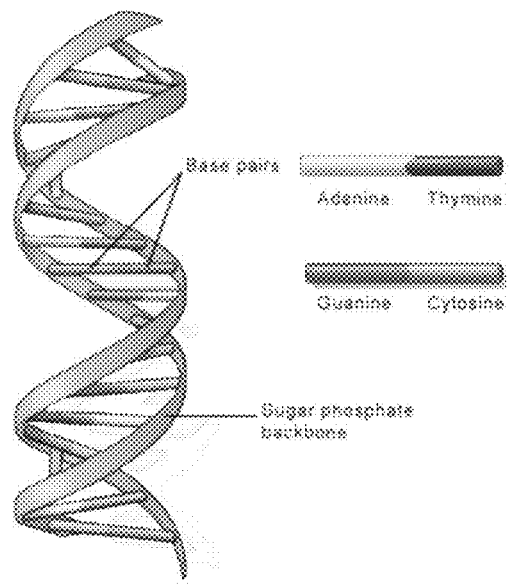
FIG. 1A shows an illustration of a segment of a double-stranded DNA helix.

Although the following detailed description contains many specifics for the purpose of illustration, a person of ordinary skill in the art will appreciate that many variations and alterations to the following details can be made and are considered included herein. Accordingly, the following embodiments are set forth without any loss of generality to, and without imposing limitations upon, any claims set forth. It is also to be understood that the terminology used herein is for describing particular embodiments only, and is not intended to be limiting. Unless defined otherwise, all technical and scientific terms used herein have the same meaning as commonly understood by one of ordinary skill in the art to which this disclosure belongs. Also, the same reference numerals in appearing in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of layouts, distances, network examples, etc., to provide a thorough understanding of various embodiments. One skilled in the relevant art will recognize, however, that such detailed embodiments do not limit the overall concepts articulated herein, but are merely representative thereof. One skilled in the relevant art will also recognize that the technology can be practiced without one or more of the specific details, or with other methods, components, layouts, etc. In other instances, well-known structures, materials, or operations may not be shown or described in detail to avoid obscuring aspects of the disclosure.

In this application, "comprises," "comprising," "containing" and "having" and the like can have the meaning ascribed to them in U.S. patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term in this written description, like "comprising" or "including," it is understood that direct support should be afforded also to "consisting essentially of" language as well as "consisting of" language as if stated explicitly and vice versa.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of phrases including "an example" or "an embodiment" in various places throughout this specification are not necessarily all referring to the same example or embodiment.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, comparative terms such as "increased," "decreased," "better," "worse," "higher," "lower," "enhanced," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a data region that has an "increased" risk of corruption can refer to a region of a memory device which is more likely to have write errors to it than other regions in the same memory device. A number of factors can cause such increased risk, including location, fabrication process, number of program pulses applied to the region, etc. In some cases, the terms "data" and "information" can be used interchangeably.

An initial overview of embodiments is provided below, and specific embodiments are then described in further detail. This initial summary is intended to aid readers in understanding the disclosure more quickly, and is not intended to identify key or essential technological features, nor is it intended to limit the scope of the claimed subject matter.

Current technologies for storing digital data include hard drives, digital tape, compact disc (CD), digital video disc (DVD), and Blu-ray Disc (BD), to name a few. Typical digital data formats store data in a binary code that is encoded, decoded, and processed on semiconductor-based computers. It is estimated that global data is doubling roughly every 2 years and will reach nearly 45 Zetta-Bytes (ZB) (45 ZB=45×$10^{21}$ bytes) by the year 2020 and 163 ZB by the year 2025. Regardless such estimations, the volume of digital data is expanding at a phenomenal rate, and will likely begin to outpace the world's ability to store such data using current memory storage technologies.

For example, based on estimates that the storage capacity of current data centers is about 1 Exa-Byte (EB) (1 EB=$10^{18}$ bytes) per data center, storage of the estimated 45 YB of data in 2040 would require at least 45,000 data centers. The costs for construction and maintenance of such high numbers of data centers would be astronomical. Additionally, current memory storage technologies require approximately 1 kg of silicon to store 75 Tera-Bytes (TB) (1 TB=$10^{12}$ bytes) of digital data. It is projected that the annual global supply of silicon wafers in the year 2040 is about $10^7$ to $10^8$ kg, which is less silicon than what would be required to store the amount of data being generated.

Figure 1B:
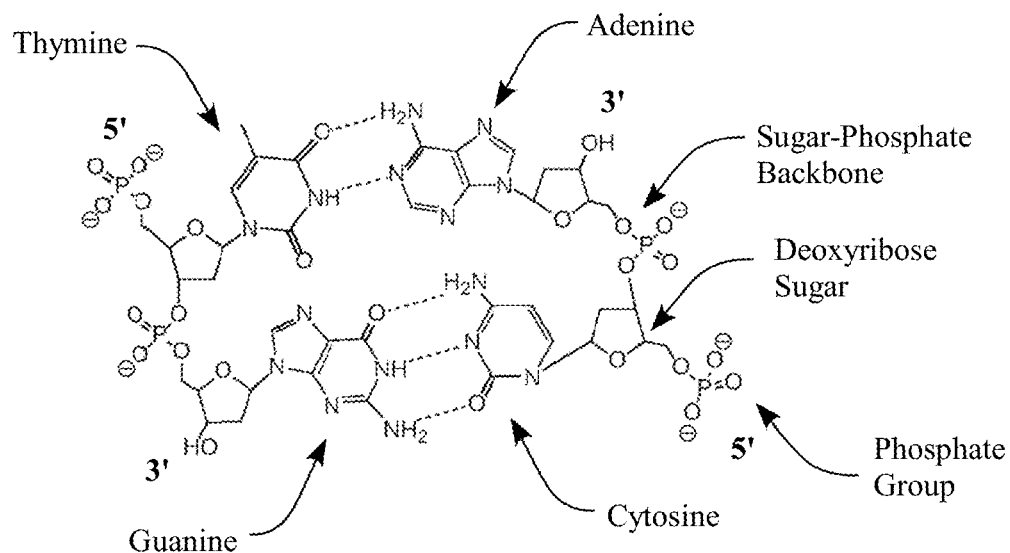
FIG. 1B shows an illustration of base pairing between nucleotides in a double-stranded DNA helix.

One alternative memory storage medium is deoxyribonucleic acid (DNA). DNA is a linear molecule of nucleotide subunits that encodes the genetic instructions necessary for the creation, development, and reproduction of all known biological organisms. These genetic instructions are encoded in the sequences of the nucleotide subunits (nucleotides) in DNA molecules. As is shown in FIG. 1A, most DNA includes two complimentary polynucleotide strands that are wound around each other to form a double helix, also known as double stranded DNA (dsDNA). As is shown in FIG. 1B, each nucleotide is made up of one of four nucleobases, cytosine (C), guanine (G), adenine (A), or thymine (T), a deoxyribose sugar, and a phosphate group. The nucleotides are joined together in a linear DNA strand by covalent bonds between the sugar of one nucleotide and the phosphate group of the next to create a sugar-phosphate backbone (see FIG. 1B). The complimentary nature of the sequences of two DNA strands in a double helix comes from base pairing rules between nucleotides that are based on hydrogen bonding, such that A pairs with T and C pairs with G. In this manner, complimentary DNA strands wind together to form stable double helix structures while non-complementary DNA strands do not. A single stranded DNA can anneal (hybridize) to another single-stranded DNA or a portion of itself to form a dsDNA helix. DNA strands anneal or hybridize following the base-pairing rule, and thus each DNA strand has a nucleotide sequence that is complimentary to the nucleotide sequence of the annealed DNA strand.

Each DNA strand molecule has a 5' end and a 3' end that is determined by the open position in the deoxyribose sugar, where typically a 5' end has an open phosphate group and a 3' end has an open hydroxyl group. In a dsDNA helix the direction of the nucleotide sequences of each strand are in an antiparallel orientation to one another, or in other words, a dsDNA helix includes one strand extending in the 5'-3' direction and the other strand extending in the 3'-5' direction. Biochemically, a DNA strand is always elongated (polymerized) in the 5'-3' direction. Chemically, a DNA strand can be elongated (polymerized) in either one of the two directions.

A single stranded DNA molecule is about 1 nm in diameter and has a spacing of about 0.34 nm between two adjacent nucleotide bases. Due to this small diameter and spacing, physical DNA is highly compressible, allowing vast amounts of information encoded in the sequence of the associated nucleotides. For example, the DNA in the largest human chromosome (chromosome 1) contains about 220 million nucleotide base pairs, but only has a linear length of 85 mm when straightened out. As such, DNA can be a highly effective medium for the storage of electronically-generated digital data or information.

The present disclosure provides data archival devices and systems capable of reliably storing massive volumes of data in an extremely compressed or compact state over centuries, millennia, or longer. Such data archival devices and systems can include a data storage phase and a data retrieval phase. As a general overview, the data storage phase includes encoding the data file in a manner that generates a compressed DNA representation that is suitable for storage. Encoding can include translating the bit sequence of the data file into a DNA sequence, compressing the DNA sequence using various compression techniques that allow for extreme compression, and storing the DNA sequence. The data retrieval phase includes retrieving the DNA sequence from storage, decompressing the DNA sequence, and decoding the DNA sequence to the original data file.

The DNA sequences described herein can be generated as physical DNA sequences or virtual DNA (VDNA) sequences using virtual genetics. Virtual genetics can include the electronic representation and manipulation of VDNA and virtual nucleotide bases (Vnbs) according to a set of virtual genetics rules, as compared to conventional (or physical) DNA, physical nucleotide bases, and manipulations thereof. While virtual genetics can follow conventional genetics rules, such is not limiting, and therefore virtual genetics can include sequences, sequence manipulations, VDNA structures, and the like, that are generally not possible in conventional genetics. For example, because DNA molecules are linear structures, the sequence order of the nucleotide bases depends on which direction the sequence is read. In conventional genetics, a DNA sequence is read from the 5' end to the 3' end. For virtual genetics purposes, however, a VDNA sequence can be read in four different ways to produce four different sequences. As described above, a dsDNA helix is comprised of two complimentary strands extending in opposite directions from one another. Since the strands are complimentary, the sequence of one strand is readily determined from knowing the sequence of the other strand. Thus, two of the four ways to read the VDNA sequence include reading each strand in the 5' to 3' direction, and the other two include reading each strand in the 3' to 5' direction. In other examples, a VDNA sequence can be read in either of these 4 directions from different starting nucleotide bases or ending at different stop nucleotide bases (i.e., frameshifting). Virtual genetics can additionally perform a variety of sequence manipulations, such as reading a sequence by skipping a fixed or varied numbers of Vnbs, the insertion or deletion (indel) in a VDNA sequence to create many different sequence variants, strand switching, sequence substitution, and the like, including combinations thereof. Such virtual manipulations can be referred to as "virtual genetics rules," which can include conventional genetics rules as well.

The encoding of a data file to DNA or VDNA can be accomplished according to various techniques and is thus not considered to be limiting. As one example, the encoding of a data file into VDNA can be accomplished by merely matching the value of each successive pair of bits in the data file bit sequence to a symbol representing the specific bit pair value. In an example of a binary bit data file, each pair of bits can have a value of 00, 01, 10, or 11. Using nucleotide bases A, T, G, and C as the symbol (or Vnb), each nucleotide can be assigned to any one of these values, the specific assignment of which is not limiting. As one example, each nucleotide base pair value can be assigned to nucleotide bases A=00, C=01, G=10, and T=11. The specific encoding of a VDNA sequence from a data file sequence can be 1:1, 1:2, 1:3, or the like. For example, in a 1:1 encoding, each Vnb corresponds to one bit of the data file sequence. In a 1:2 encoding, each Vnb corresponds to a pair of bits of the data file sequence, or in other words, a Vnb corresponds to the numeric value of a pair of bits, and so on. In some cases, more complex encoding can be utilized. For example, a VDNA sequence can be encoded in a manner that optimizes or reduces GC content, homopolymers, and the like. FIGS. 2A-2E show one nonlimiting technique for encoding a data file sequence that results in a VDNA sequence having a GC content of around 50% and no more than 2 of the same nucleotide bases in a row, or in other words, it eliminates homopolymers of 3 or more. FIG. 2A shows a data file having a binary bit sequence partitioned into 8-digit divisions. The number of digits per division is merely exemplary, and any useful division is considered to be within the present scope. In some examples a division can be referred to as a byte-unit, which can include any number of digits. Additionally, various numbers of Vnbs can be used to represent the bit sequence of each division. In the present example technique, the 8 digits of each bit sequence division is represented by 6 Vnbs, which allows a degree of redundancy to account for any modifications due to G/C content or homopolymer reduction.

FIG. 2B shows a pattern of alignment between the 6 VDNA digits (x) and the 8 binary digits (y). For example, VDNA digits 1, 3, 4, and 6 each encodes for a single binary digit, namely binary digits 1, 4, 5, and 8, respectively. VDNA digits 2 and 5 encode for double digits, namely binary digits 2 and 3 for VDNA digit 2 and binary digits 6 and 7 for VDNA digit 5. The specific encoding of the first two divisions of the data file is shown in FIG. 2C, where the 6 VDNA digits are show with the corresponding binary digit values. The single-digit table and the double-digit table shown in FIG. 2D can be used to determine the correspondence between the Vnbs of the VDNA and the values of the binary bits for a given digit position of a division. According to the single-digit table, a single binary digit having a value of 0 will be encoded by either A or G and a single binary digit having a value of 1 will be encoded by either T or C. Which Vnb is used to encode a given single binary digit depends on the preceding Vnb. According to the double-digit table, each Vnb corresponds to a given double digit value, regardless of the preceding Vnb. It is noted that the actual correspondence between specific Vnbs (which can also be other symbols, such as other nucleotide bases) and the values shown in each table is merely exemplary. Referencing the first division shown on the left in FIG. 2C, for example, the first VDNA digit is a single digit and the first binary bit value is 0. For the initial division of a binary bit sequence, the Vnb can be arbitrarily selected as either A or G because there is no preceding Vnb in this case. For the example shown in FIG. 2C, A is chosen. The second VDNA digit is a double digit corresponding to binary digits 2 and 3 that have a bit value of 10, which according to the double-digit table is encoded by G. The third and fourth VDNA digits corresponding to binary digits 4 and 5 are both single digits having binary bit values of 0 and 1, respectively. The Vnb preceding VDNA digit 3 is G, so the Vnb encoding a 0 at this position is A. The Vnb preceding VDNA digit 4 is A, so the Vnb encoding a 1 at this position is C. VDNA digit 5 is a double digit corresponding to binary digits 6 and 7, which have a bit value of 00. As per the double-digit table, a 00 value corresponds to A. VDNA digit 6, the last digit in the first division, corresponds to binary digit 8, which has a bit value of 1. The Vnb preceding VDNA digit 6 is A, so the Vnb encoding a 1 at this position is C. For the next division, the preceding Vnb is C and the bit value is 0, so the first VDNA digit is A. This process is repeated until the data file has been encoded to a VDNA sequence, as is shown in FIG. 2E. It is noted that the encoding scheme can be embodied in various ways such as, for example, a lookup table.

Figure 3:
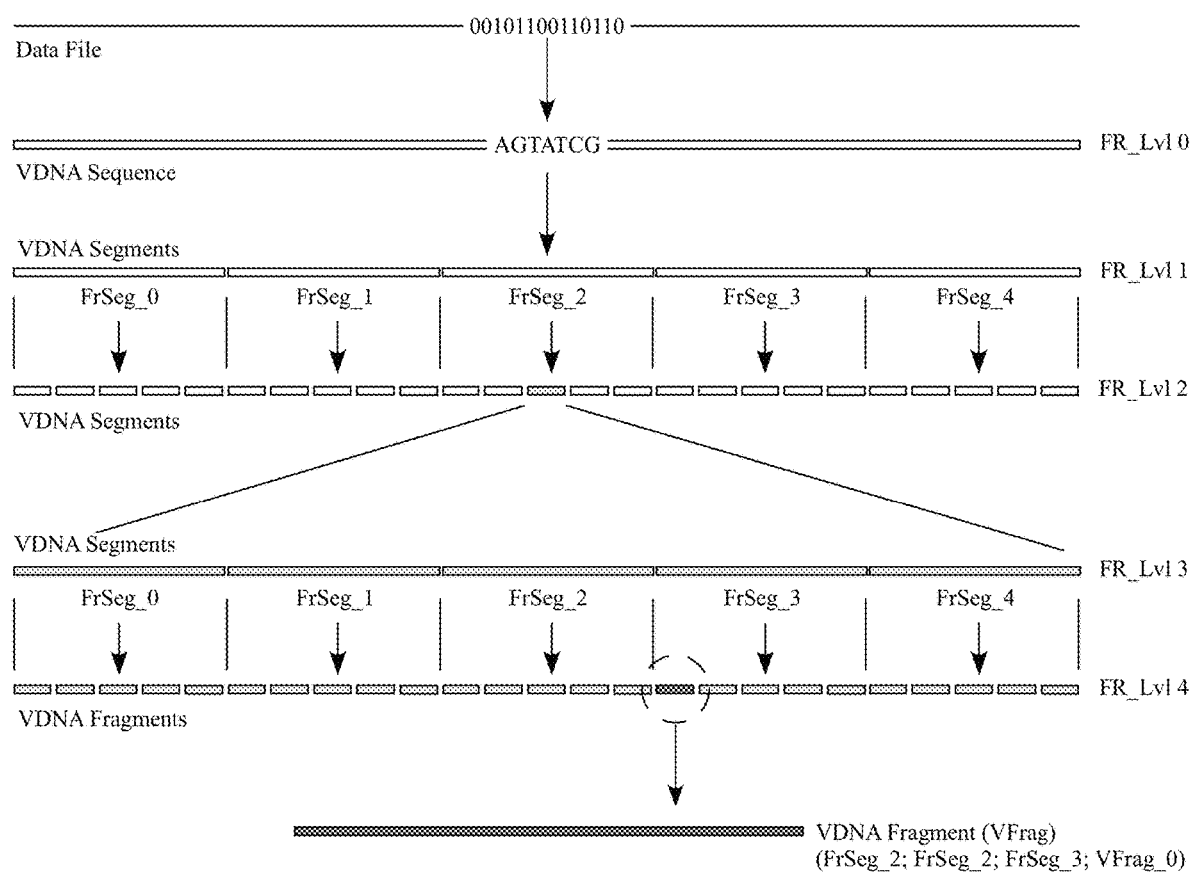
FIG. 3 shows an illustration of the fragmentation of VDNA sequence through multiple fragmentation levels to a VDNA fragment in accordance with an example embodiment.

Once generated, the VDNA sequence can be fragmented into multiple VDNA segments or fragments that are of a size that are more manageable, both for virtual and physical DNA manipulation. The VDNA sequence can be fragmented into any size of segments or fragments, depending on the size of the VDNA sequence. In one example, such fragmentation can be performed once on the VDNA sequence to generate multiple VDNA fragments. In another example, the VDNA sequence can be fragmented into multiple VDNA segments that are each further fragmented into multiple VDNA fragments. The fragmentation of the VDNA segments can be performed once or multiple times to generate the VDNA fragments. Each fragmentation occurrence can be described as a fragmentation level, shown in FIG. 3 as Fr_Lvl n, where n is the number of times the VDNA sequence, or products therefrom, have been fragmented. In FIG. 3, the VDNA sequence is shown with a FrLvl_0, meaning that the VDNA sequence has not been fragmented. Following initial fragmentation (FrLvl_1), the VDNA sequence is shown divided into multiple VDNA segments, FrSeg_(0-4), with a final fragmentation (FrLvl_4) showing one VDNA segment divided into multiple VDNA fragments (VFrag_(0-4)). As such, each of these VDNA segments and fragments can be mapped to the VDNA sequence according to fragmentation level and segment/fragment number. This process can be performed any number of times to generate VDNA fragments of any size. In one example, VDNA fragments can be generated having a size from 100 Vnb to 100,000 Vnb. In another example, VDNA fragments can be generated having a size from 100 Vnb to 50,000 Vnb. In yet another example, VDNA fragments can be generated having a size from 100 Vnb to 10,000 Vnb. In a further example, VDNA fragments can be generated having a size from 100 Vnb to 5,000 Vnb, or from 100 Vnb to 2,000 Vnb.

For a more specific description of the example shown in FIG. 3, the VDNA sequence is fragmented into a plurality of VDNA segments at FrLvl_1, which are then further fragmented into another plurality of smaller VDNA segments at FrLvl_2. The VDNA segments at FrLvl_2 are further fragmented at FrLvl_3 into yet another plurality of smaller VDNA segments. It is noted that only a single VDNA segment is shown being fragmented at FrLvl_3 for illustration purposes. The VDNA sequences shown at FrLvl_3 are fragmented at FrLvl_4 into a plurality of VDNA fragments. The products of the final level of fragmentation are referred to as VDNA fragments, regardless of how many times the VDNA sequence and subdivisions of segments have been fragmented. Each final fragmentation-level VDNA fragment can be represented by a short sequence of Vnbs referred to herein as an index sequence (Idx_SEQ), which indexes the position of the associated VDNA fragment at each fragmentation level. The size of the Idx_SEQ can vary depending on the size of the unfragmented VDNA sequence, the number of fragmentation levels performed on the VDNA sequence, the encoding system design, and the like. In some examples the Idx_SEQ can range from 10 Vnbs to 50 Vnbs or more in size. In other examples, the Idx_SEQ can range from 10 Vnbs to 30 Vnbs in size. In one specific example, the Idx_SEQ can be 20 Vnbs in size. As one implementation of this example, the Idx_SEQ can be divided into 4 units of 5 Vnbs, where the first unit can be used to identify the VDNA segment containing the VDNA fragment at FrLvl_1, the second unit can be used to identify the VDNA segment containing the VDNA fragment at FrLvl_2, and so on. In other words, the position of the unit represents the FrLvl (for a total of 4 levels using 4 units in this example), and the value of the unit represents the position of the VDNA segment containing the VDNA fragment within the FrLvl. In one example of an Idx_SEQ where each Vnb digit can take one of 3 values (to avoid homopolymers), a total of $3^5$ possible sequences can be encoded for each level. Thus applying a 20 digit Idx_SEQ to the VDNA fragment shown at the bottom of FIG. 3 allows the mapping of the fragment to its original position in the VDNA sequence according to its position at each level of fragmentation, which in this case would be FrLvl_1:FrSeg_2, FrLvl_2:FrSeg_2, FrLvl_3:FrSeg_3, FrLvl_4:VFrag_0 (or FrSeg_2; FrSeg_2; FrSeg_3;

VFrag_0). As such, a 20-digit Idx_SEQ will allow a VDNA sequence to be divided into $(3^5)^4$ fragments, which is sufficient for a binary file in the Tera-byte range, assuming each fragment is >1000 Vnb. The original VDNA sequence can be reconstructed from the Idx_SEQs of all VDNA fragments resulting from that VDNA sequence's fragmentation. In addition, any VDNA segment at any level of fragmentation can be reconstructed from the collection of VDNA fragments and the associated Idx_SEQs. It is noted that the mapping scheme of the segments and fragments of the VDNA sequence is not limiting, and the preceding is merely exemplary.

Figure 4A:
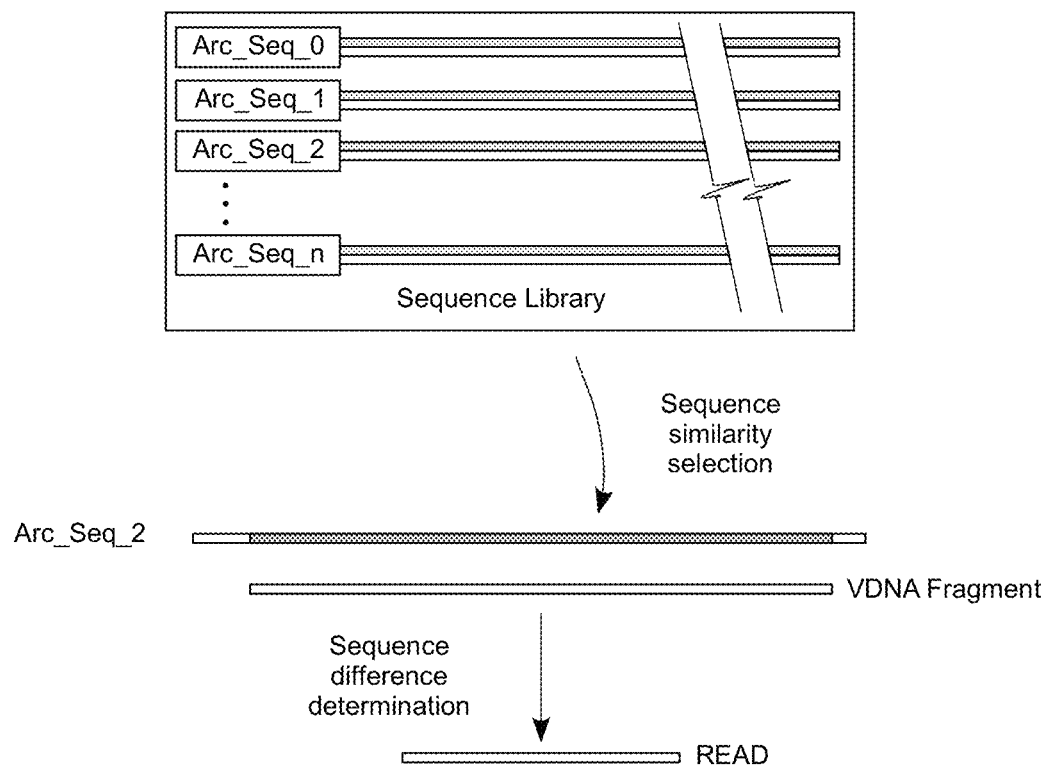
FIG. 4A shows an illustration of a READ sequence generated from a VDNA fragment sequence and an Arc_SEQ in accordance with an example embodiment.

Once a VDNA fragment has been generated it can be reduced in size through various compression techniques. It can be beneficial for the compression of the VDNA fragment to be lossless, or in other words, a compression process that allows the complete reconstruction of the compressed sequence with no loss of sequence information. While any compression technique is considered to be within the present scope, however, in some cases the compression technique can be lossless. One example of a lossless compression technique suitable for DNA and VDNA sequence compression is a reference-based sequence compression. Reference-based compression stores only the sequence differences between a known reference sequence and the sequence being compressed. The sequence differences can then be applied to the known reference sequence to regenerate the original uncompressed sequence. In the present case, for example, reference-based sequence compression can be accomplished by storing the sequence differences between a VDNA fragment and a known archive sequence (Arc_SEQ), which can then be used to regenerate the VDNA fragment sequence from the Arc_SEQ. As is shown in FIG. 4A, an Arc_SEQ is selected from a sequence library based on sequence similarity to the VDNA fragment. For example, a sequence alignment process can be performed between the VDNA fragment and Arc_SEQs or portions of Arc_SEQs within the sequence library. In some implementations, the Arc_SEQ having the highest sequence alignment with the VDNA fragment can be selected. In other implementations, any Arc_SEQ having a sequence alignment with the VDNA fragment that is above a sequence alignment threshold with the VDNA fragment can be selected. It is noted that a greater sequence similarity between an Arc_SEQ and a VDNA fragment will generally result in a greater degree of reference-based compression.

For the example shown in FIG. 4A, Arc_SEQ_2 is selected from the sequence library and associated with the VDNA fragment. The sequence differences between Arc_SEQ_2 and the VDNA fragment are then determined according to various virtual genetics rules, and a read (READ) sequence is created that includes instructions to regenerate the VDNA fragment from the Arc_SEQ (e.g. Arc_SEQ_2 in this case) given the sequence differences. The Arc_SEQ can include a codename to provide a link between the Arc_SEQ and any VDNA fragment associated therewith. As such, the codename provides the appropriate Arc_SEQ upon which the READ sequence is used to derive the VDNA fragment according to the aforementioned sequence differences. It is noted that the sequence library can include VDNA Arc_SEQs or physical DNA Arc_SEQs. A codename can be a DNA or VDNA sequence of any length that can be used to reference an Arc_SEQ, such as, for example, from 10 nt to 50 nt, from 50 nt to 100 nt, from 100 nt to 200 nt, from 200 nt to 500 nt, or more. Assuming each nucleotide digit has 3 values to avoid homopolymers, a 100 nt codename system can code for $3^{100}$ different Arc_SEQs. In other words, such a 100 nt codename can reference a library having $3^{100}$ Arc_SEQs.

Figure 4B:
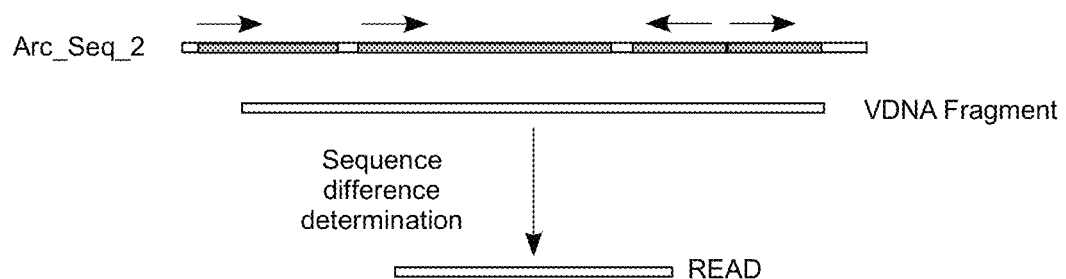
FIG. 4B shows an illustration of a READ sequence generated from a VDNA fragment sequence and an Arc_SEQ in accordance with an example embodiment.

The READ sequence is thus a set of instructions for decoding/reading the Arc_SEQ to regenerate the VDNA fragment. FIG. 4A shows an example of an Arc_SEQ as a continuous sequence, and as such, the READ sequence would provide instructions on how to read the continuous Arc_SEQ in order to regenerate the VDNA fragment. It is noted, however, that the Arc_SEQ may include discontinuous sequence portions, even including portions located on a complimentary strand of the Arc_SEQ. FIG. 4B for example, illustrates several discontinuous sequence portions of Arc_SEQ_2. The arrows in FIG. 4B depict the read direction of each sequence portion, with one portion being shown as having a read direction opposite to the other sequence portions. It is noted that sequence reading in opposite directions (5'-3' and 3'-5') on the same strand is not generally possible for physical DNA sequences. As such, opposite read direction sequences relates to VDNA sequences where such can be used to derive a portion of the VDNA fragment from the Arc_SEQ. It is also contemplated that a portion of the Arc_SEQ can be derived from a complimentary strand. In addition to read direction and the use of either Arc_SEQ strand, Arc_SEQ portions can be read using different starting points, including starting points within other portions of the Arc_SEQ, with or without frameshifting. The virtual genetics rules used to generate the READ sequence can also utilize a variety of sequence manipulations to create many different sequence variants in the characterization of the differences between the VDNA fragment and the Arc_SEQ, including insertions or deletions (indel), strand switching, sequence substitution, and the like, including combinations thereof.

The following is a nonlimiting example of reference compression, where a set of instructions (READ, Fx) is used to regenerate a VDNA fragment from an Arc_SEQ.

```
F1:
(p1, l1, z1) = (1, 4, C),

F2:
(p2, l2, z2) = (6, 6, T),

F3:
(p3, l3, z3) = (12, 5, C),

F4:
(p4, l4, z4) = (14, 2, T)

Arc_SEQ:
                                    (SEQ ID NO: 01)
AATGTA₆ GGTACA₁₂ TAAGAT₁₈ GCTAGA₂₄ ...

VDNA fragment:
                                    (SEQ ID NO: 02)
AATGCA GGTACT ATAAGC AAT ...
```

In the instruction set, p is the location of the starting Vnb (or nucleotide base) in the Arc_SEQ, l is the length of a sequence starting at p that is the same between the Arc_SEQ and the VDNA fragment, and z is a Vnb (or nucleotide base) that is different between Arc_SEQ and VDNA fragment, or in other words, z is the Vnb that is being encoded in the instruction. The encoded Vnbs are shown in bold in the VDNA fragment above. Keeping in mind that the instructions only encode the differences between the two sequences, the starting Vnb and the sequence length represent a sequence portion that is the same between the two sequences. For the first instruction F1, the location of the starting Vnb is 1, the sequence length is 4, so the similar sequence portion of F1 is AATG. The encoded Vnb of F1 is C, so F1 decodes to AATGC. For F2 the start location is 6 and the sequence length is 6, which in this case is AGGTAC. The encoded Vnb is T, so F2 decodes as AGGTACT, which gives AATGCA$_6$ GGTACT$_{12}$ (SEQ ID NO: 03) for the F1 and F2 instructions. Continuing on, the F3 start location is 12 and the sequence length is 5, which is ATAAG. The encoded Vnb is C, so F3 decodes to ATAAGC. For F4 the start location is 14 and the sequence length is 2, which is AA. The encoded Vnb is T, so F4 decodes to AAT, which is appended to F3. Note that the sequence for F4 is taken from within the sequence of F3. As such, the READ sequence of instructions and the Arc_SEQ are sufficient to reconstruct VDNA fragment in a lossless manner. Substitutions may represent a large proportion of the differences between two sequences, which will reduce the number of encoded differences that need to be stored. With this in mind, the selection of the Arc_SEQ can affect the level of compression achieved by, for example, biasing the selection toward substitutions.

Figure 5A:
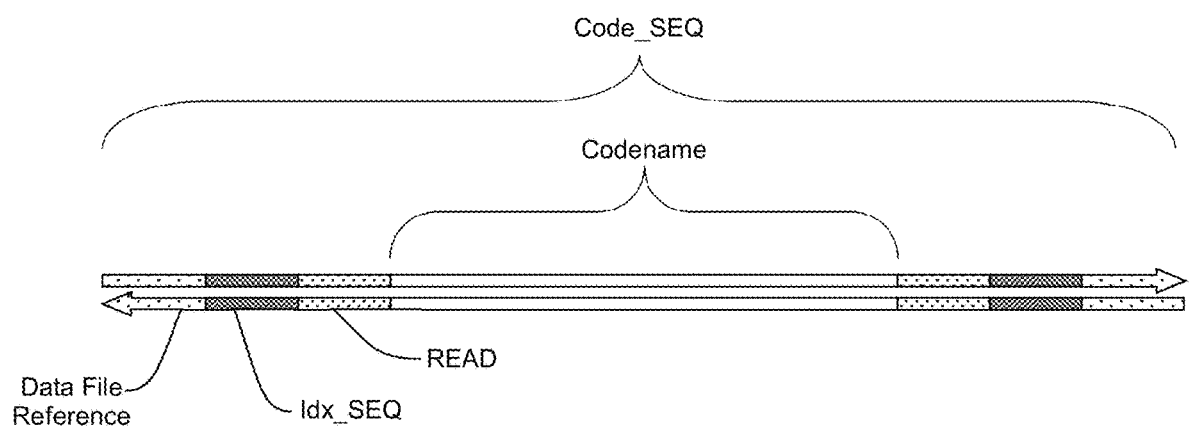
FIG. 5A shows an illustration of a Code_SEQ in accordance with an example embodiment.

In order to utilize DNA as a storage medium, the information needed to regenerate the VDNA sequence and the data file are written as a physical DNA sequence. FIG. 5A, for example, illustrates a codeword sequence (Code_SEQ) that can either be generated as a VDNA sequence that is used as a template to generate the DNA sequence or generated directly as a DNA sequence. The Code_SEQ can include any information to facilitate the regeneration of the data file, as well as any information relating to the nature of the data file, the various sequences along the encoding/fragmentation/compression hierarchy, and the like, archival information, general reconstruction instructions, and the like. Additionally, the organization of the various sections of the Code_SEQ shown in FIG. 5A is merely for illustration and is not limiting. It is additionally noted that the Code_SEQ is shown as with a complimentary strand. While double-stranded DNA is generally considered to be more stable than single-stranded DNA, the present scope includes Code_SEQ implementations of single-stranded DNA.

Figure 5B:
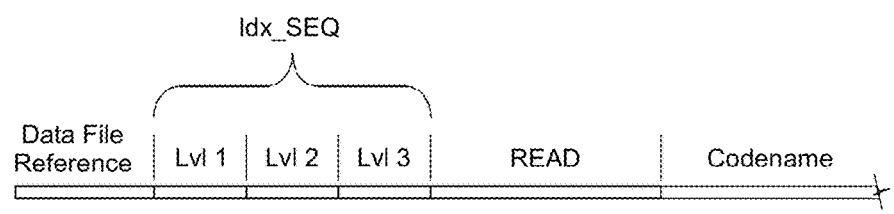
FIG. 5B shows an illustration of a portion of a Code_SEQ in accordance with an example embodiment.

The Code_SEQ shown in FIG. 5A includes a sequence representation of the codename used to identify the Arc_SEQ, along with the READ sequence encoding the differences between the associated VDNA fragment and the associated Arc_SEQ to facilitate regeneration of the VDNA fragment. The Code_SEQ additionally comprises the Idx_SEQ that includes the indexing of the associated VDNA fragment in the VDNA sequence. In some examples the idx_SEQ can additionally include indexing or other reconstruction information pertaining to other VDNA fragments and/or the VDNA sequence in part or as a whole. In some examples, the idx_SEQ can include the original position of the VDNA fragment at each level of fragmentation of the VDNA sequence. As one specific example case, FIG. 5B shows the Idx_SEQ subdivided by fragmentation level, which can include, without limitation, the identity of the source VDNA segment and relative position for the VDNA fragment at each fragmentation level. FIGS. 5A & B additionally show a data file reference section, which can include various forms of information referenced to the data file. In one example the data file reference section can include DNA primers specific to the data file, a portion of the data file, multiple data files such as associated data files, and the like. DNA primers are used to replicate and amplify the appropriate Code_SEQ(s) to regenerate the data file(s) from a common pool of Code_SEQs associated with various other data files. As another example, a VDNA fragment can be associated with multiple Arc_SEQ sequences. In this case, a Code_SEQ can have multiple codenames, each of which is associated with its own READ. These READ sequences can specify the orientations (by 2 nt digits), the start positions (5 to 10 nt digits) and the end positions (5 to 10 nt digit) of the associated portions of the encoded VDNA fragment on different Arc_SEQs that are identified via each codename associated with each READ. As one simplified example, such a Code_SEQ can include a data file reference, an Idx_SEQ, a READ1, a Codename1, a READ2, a Codename2, and so on. In an alternative example, a Code_SEQ can have one codename for an Arc_SEQ and multiple READs, as is shown in FIG. 4B.

Figure 6A:
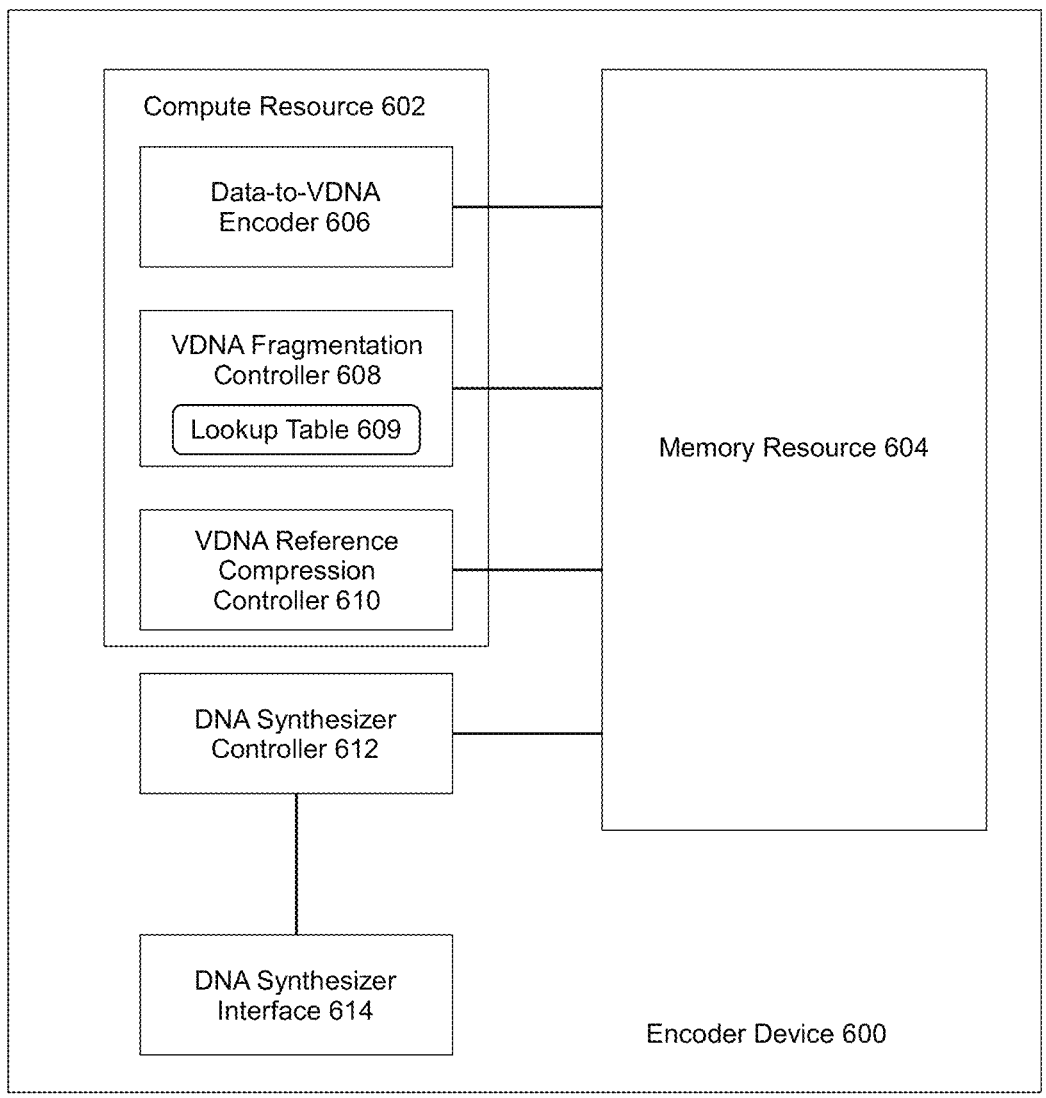
FIG. 6A shows a block diagram of an encoder device in accordance with an example embodiment.

In one example shown in FIG. 6A, an encoder device 600 includes a compute resource 602 having a number of encoder functions. It is noted that these various functions can be distinct elements of the compute resource 602, distinct and separate elements from the compute resource 602, functions performed by the compute resource 602, or the like. The compute resource 602 can include any type of control unit, processor, or the like, that is capable of performing the VDNA processing and manipulations needed to encode a data file as DNA. As used herein, the term "processor" can include a single processor or multiple processors, including single core processors and multi-core processors. A processor can include general purpose processors, specialized processors such as central processing units (CPUs), graphics processing units (GPUs), digital signal processors (DSPs), microcontrollers (MCUs), microprocessors, embedded controllers (ECs), embedded processors, field programmable gate arrays (FPGAs), network processors, application-specific instruction set processors (ASIPs), application-specific integrated circuit (ASIC) processors, co-processors, and the like as well as other types of specialized processors. Additionally, a processor can be packaged in numerous configurations, which is not limiting. For example, a processor can be packaged in a common processor package, a multi-core processor package, a system-on-chip (SoC) package, a system-in-package (SiP) package, a system-on-package (SOP) package, and the like.

The encoder device 600 can additionally include a memory resource 604, which can be physically incorporated into the device or removably coupled thereto via a memory resource interface. In some examples the memory resource 604 can be utilized to hold the VDNA sequence, segments, fragments, and/or the like during the encoding process. In other examples the memory resource 604 can be utilized for longer-term storage of VDNA sequence, segments, fragments, and/or the like, as well as other information related to the encoding process. As such, the memory resource 604 can be volatile or nonvolatile, depending on the design of the encoder device 600 and its intended use. Additionally, the memory resource 604 can represent both volatile and non-volatile memory, as well as memory that can function as either memory type. The memory can hold the lookup tables for encoding and decoding as well as virtual genetics rules or other defined rules.

Volatile memory, for example, is a memory medium that requires power to maintain the state of data stored by the medium. Volatile memory can include any type of volatile memory, nonlimiting examples of which can include random access memory (RAM), such as static random-access memory (SRAM), dynamic random-access memory (DRAM), synchronous dynamic random-access memory (SDRAM), and the like, including combinations thereof. SDRAM memory can include any variant thereof, such as single data rate SDRAM (SDR DRAM), double data rate (DDR) SDRAM, including DDR, DDR2, DDR3, DDR4, DDR5, and so on, described collectively as DDRx, and low power DDR (LPDDR) SDRAM, including LPDDR, LPDDR2, LPDDR3, LPDDR4, and so on, described collectively as LPDDRx. In some examples, DRAM complies with a standard promulgated by JEDEC, such as JESD79F for DDR SDRAM, JESD79-2F for DDR2 SDRAM, JESD79-3F for DDR3 SDRAM, JESD79-4A for DDR4 SDRAM, JESD209B for LPDDR SDRAM, JESD209-2F for LPDDR2 SDRAM, JESD209-3C for LPDDR3 SDRAM, and JESD209-4A for LPDDR4 SDRAM (these standards are available at www.jedec.org; DDR5 SDRAM is forthcoming). Such standards (and similar standards) may be referred to as DDR-based or LPDDR-based standards, and communication interfaces that implement such standards may be referred to as DDR-based or LPDDR-based interfaces. In one specific example, the volatile memory can be DRAM. In another specific example, the volatile memory can be DDRx SDRAM. In yet another specific aspect, the volatile memory can be LPDDRx SDRAM.

Nonvolatile memory (NVM) is a storage medium that does not require power to maintain the state of data stored by the medium. NVM has traditionally been used for the task of data storage, or long-term persistent storage, but new and evolving memory technologies allow the use of some NVM technologies in roles that extend beyond traditional data storage. One example of such a role is the use of NVM as main or system memory. Nonvolatile system memory (NVMsys) can combine data reliability of traditional storage with low latency and high bandwidth performance, having many advantages over traditional volatile memory, such as high density, large capacity, lower power consumption, and reduced manufacturing complexity, to name a few. Byte-addressable, write-in-place NVM such as three-dimensional (3D) cross-point memory, for example, can operate as byte-addressable memory similar to dynamic random-access memory (DRAM), or as block-addressable memory similar to NAND flash. In other words, such NVM can operate as system memory or as persistent storage memory (NVMstor). In some situations where NVM is functioning as system memory, stored data can be discarded or otherwise rendered unreadable when power to the NVMsys is interrupted. NVMsys also allows increased flexibility in data management by providing non-volatile, low-latency memory that can be located closer to a processor in a computing device. In some examples, NVMsys can reside on a DRAM bus, such that the NVMsys can provide ultra-fast DRAM-like access to data. NVMsys can also be useful in computing environments that frequently access large, complex data sets, and environments that are sensitive to downtime caused by power failures or system crashes.

Nonlimiting examples of NVM can include planar or 3D NAND flash memory, including single or multi-threshold-level NAND flash memory, NOR flash memory, single or multi-level phase change memory (PCM), such as chalcogenide glass PCM, planar or 3D PCM, cross-point array memory, including 3D cross-point memory, non-volatile dual in-line memory module (NVDIMM)-based memory, such as flash-based (NVDIMM-F) memory, flash/DRAM-based (NVDIMM-N) memory, persistent memory-based (NVDIMM-P) memory, 3D cross-point-based NVDIMM memory, resistive RAM (ReRAM), including metal-oxide- or oxygen vacancy-based ReRAM, such as HfO2-, Hf/HfOx-, Ti/HfO2-, TiOx-, and TaOx-based ReRAM, filament-based ReRAM, such as Ag/GeS2-, ZrTe/Al2O3-, and Ag-based ReRAM, programmable metallization cell (PMC) memory, such as conductive-bridging RAM (CBRAM), silicon-oxide-nitride-oxide-silicon (SONOS) memory, ferroelectric RAM (FeRAM), ferroelectric transistor RAM (Fe-TRAM), anti-ferroelectric memory, polymer memory (e.g., ferroelectric polymer memory), magnetoresistive RAM (MRAM), write-in-place non-volatile MRAM (NVM-RAM), spin-transfer torque (STT) memory, spin-orbit torque (SOT) memory, nanowire memory, electrically erasable programmable read-only memory (EEPROM), nanotube RAM (NRAM), other memristor- and thyristor-based memory, spintronic magnetic junction-based memory, magnetic tunneling junction (MTJ)-based memory, domain wall (DW)-based memory, and the like, including combinations thereof. The term "memory device" can refer to the die itself and/or to a packaged memory product. NVM can be byte or block addressable. In some examples, NVM can comply with one or more standards promulgated by the Joint Electron Device Engineering Council (JEDEC), such as JESD21-C, JESD218, JESD219, JESD220-1, JESD223B, JESD223-1, or other suitable standard (the JEDEC standards cited herein are available at www.jedec.org). In one specific example, the NVM can be 3D cross-point memory.

In one example, the compute resource 602 can include a data-to-VDNA encoder 606 functionally coupled to the memory resource 604. The data-to-VDNA encoder 606 generates the a VDNA sequence of Vnbs that reversibly encodes the bit sequence of the data file, which can involve encoding operations on the data file in the memory resource 604 or encoding operations on portions of the data file sent back and forth between the data-to-VDNA encoder 606 and the memory resource 604. The compute resource 602 can also include a VDNA fragmentation controller 608, which fragments the VDNA sequence into VDNA segments and/or VDNA fragments through at least one fragmentation level. The fragmentation controller 608 can also index the various VDNA segments and/or fragments to facilitate the reconstruction of the VDNA sequence. In some cases, the fragmentation controller 608 can include a lookup table 609 of the index mapping to the VDNA segments and/or fragments. The lookup table 609 can be located in the VDNA fragmentation controller 608 or apart from the VDNA fragmentation controller 608. The compute resource 602 can also include a VDNA reference-compression controller 610 to compress VDNA fragments by, for example, the reference compression technique described above.

The encoder device 600 can, in some examples, further include a DNA synthesizer controller 612 coupled to a DNA synthesizer interface 614. The DNA synthesizer controller 612 can be a separate controller from the compute resource 602 as shown, or it can be integrated as part of the compute resource (not shown). The DNA synthesizer controller 612 is configured to receive the sequence information to be used to generate the Code_SEQ, from the memory resource 604, directly from the VDNA reference-compression controller (not shown), or from any other memory location where such sequence information has been stored.

Figure 6B:
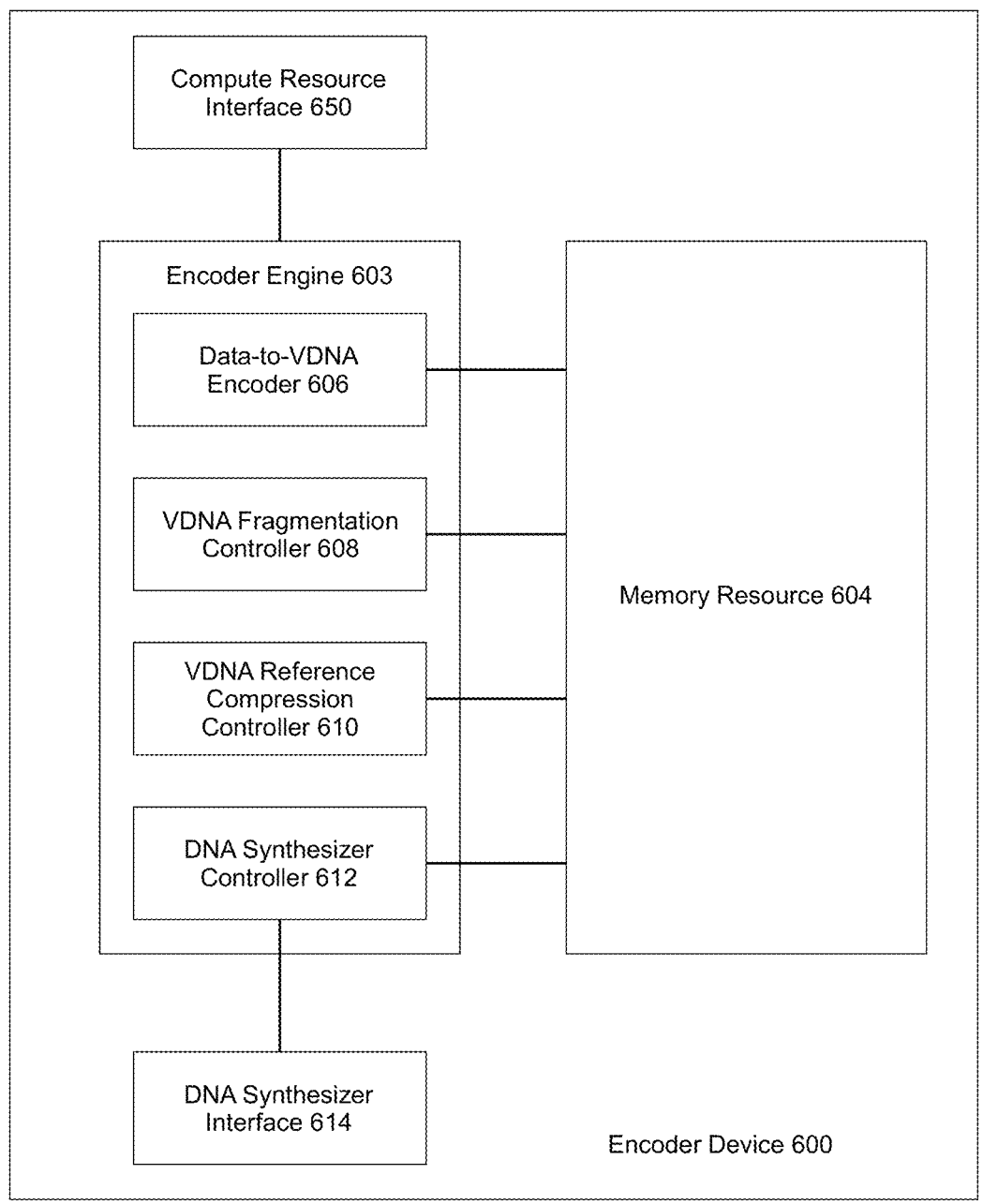
FIG. 6B shows a block diagram of an encoder device in accordance with an example embodiment.

FIG. 6B illustrates a similar example of an encoder device that includes an encoder engine 603 and a compute resource interface 650 through which the encoder engine 603 and a compute resource communicate. Embodiment examples are also contemplated where the encoder engine is integrated with the compute resource in the encoder device, the encoder engine and the compute resource are distinct and both present in the encoder device, and the like. Additionally, the encoder engine can be a processor as described above. The DNA synthesizer controller 612 can be an integrated element of the encoder engine 603 as is shown in FIG. 6B, or the DNA synthesizer controller can be a distinct element apart from, but communicatively coupled to, the encoder engine.

Figure 7:
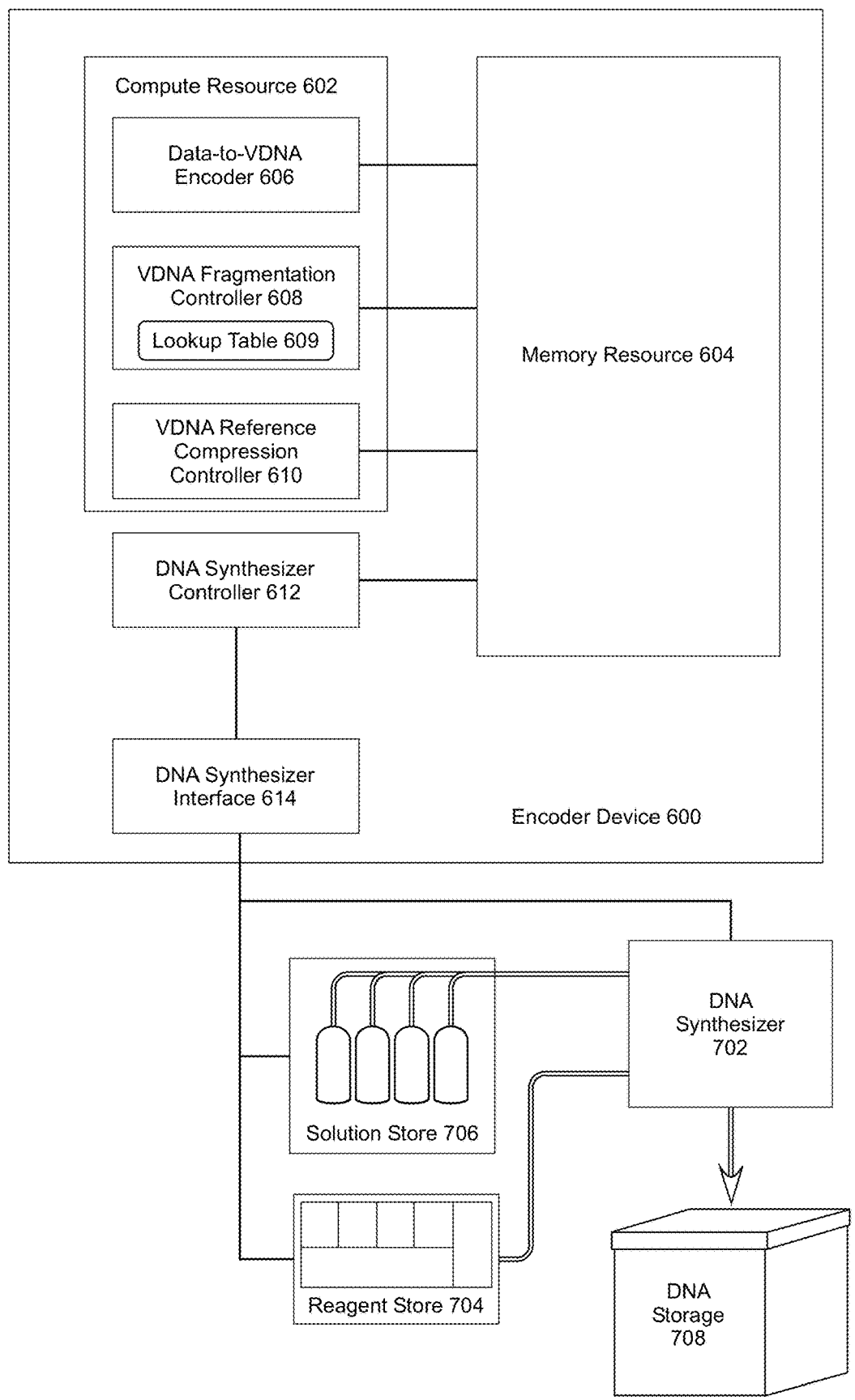
FIG. 7 shows a block diagram of a DNA data storage system in accordance with an example embodiment.

FIG. 7 shows an example of a DNA data storage system that includes an encoder device 600 similar to the example of FIG. 6A and a DNA synthesizer 702 communicatively coupled to the DNA synthesizer interface 614. The DNA synthesizer 702 receives instructions from the DNA synthesizer controller 612 through the DNA synthesizer interface 614 to generate specific DNA sequences, such as for example, a Code_SEQ corresponding to an encoded data file. A reagent store 704 can be functionally coupled to the DNA synthesizer 702 to provide various reagents used to synthesize DNA. Additionally, a solution store 706 can be functionally coupled to the DNA synthesizer 702 to provide various solutions used to synthesize DNA. In some examples, the Code_SEQ can be generated as a VDNA Code_SEQ and subsequently sent to the DNA synthesizer controller 612. In other examples, at least one of the codename, READ, Idx_SEQ, and data file reference sequences is sent separately to the DNA synthesizer controller 612 for incorporation into the Code_SEQ as physical DNA. In yet other examples, portions of Code_SEQs can be pre-generated and stored in a Code_SEQ library, either as VDNA or DNA, each including at least a codename of a corresponding Arc_SEQ. Once the READ has been generated from a VDNA fragment and an Arc_SEQ, a Code_SEQ specific to the Arc_SEQ codename is selected and sent to the DNA synthesizer controller where the READ, Idx_SEQ, and data file reference sequences are added.

Once the Code_SEQ has been generated as a DNA sequence, further processing can be performed in some cases. For example, the code sequence can be amplified using a PCR process to increase the quantity of the Code_SEQ DNA prior to storage. In another example, the accuracy of the Code_SEQ can be verified by sequencing the DNA in, for example, a DNA sequencer. Additionally, the Code_SEQ can be prepared for cold storage by washing to remove any elements that may potentially degrade the DNA over time. Further preparation of the DNA can vary depending on the cold storage conditions and the time period over which the Code_SEQ is to be stored. In some cases, for example, the DNA can be suspended in a tris(hydroxymethyl)aminomethane-ethylenediaminetetraacetic acid (Tris-EDTA) buffer. As a longer-term storage solution, the DNA can be precipitated and stored in an alcohol solution, such as ethanol for example. As another example, the DNA can be precipitated and stored dried.

The DNA storage system can also include a DNA storage 708, into which the Code_SEQ can be transferred for storage. In one example, the DNA storage 708 can be a low temperature DNA storage, such as a −80° C. or lower temperature storage. The actual temperature at which the Code_SEQ can be stored can vary, provided the temperature is sufficiently low to prevent DNA degradation over the storage time period. Other nonlimiting examples of storage temperatures can include −100° C. or lower, −120° C. or lower, −140° C. or lower, or −160° C. or lower. The Code_SEQ can be transferred to the DNA storage 708 in a variety of nonlimiting ways. For example, the Code_SEQ can be loaded into a storage receptacle, tube, or the like, which can be transferred to the DNA storage 708 mechanically, by human transport, or the like. Synthesized DNA can be pooled, many pools can be stored in an array of tubes or in wells in a plate. The plate or array can have barcodes or the like for automated operation. In another example, the Code_SEQ can be transferred to a storage receptacle in the DNA storage 708 via a fluidic system for subsequent freezing. Regardless of the method of transport, the Code_SEQ can be discreetly contained in a dedicated storage receptacle or contained in a storage receptacle with other different Code_SEQs. In some cases, Code_SEQs contained in a common storage receptacle can be associated by data file or related sets of data files. In other cases, Code_SEQs contained in a common storage receptacle can be unrelated. As has been described above, Code_SEQs can be located using associated DNA primers that can be specific to a single Code_SEQ, to all Code_SEQs from a specific fragmentation level of a data file, to all Code_SEQs of a data file, to all Code_SEQs of an associated set of data files, or the like. As such, one or more specific Code_SEQs can readily be retrieved from a common pool of unrelated Code_SEQs.

DNA synthesis can be accomplished by a variety of techniques using a variety of DNA synthesizer designs, which are not limiting. In one example, a phosphoramidite chemistry technique can be utilized that includes a four-step DNA oligonucleotide (DNA sequence) synthesis process. Phosphoramidite chemistry can be accomplished using a column-based solid-phase, a well-plate solid-phase, a flat surface ink-jet based processes, or the like, depending on the amount of material (nmol to μmol) and number of different sequences to be synthesized. Initially, a dimethoxytrityl (DMT)-protected nucleoside phosphoramidite attached to a support surface is deprotected using an acid. Next, the unprotected 5' OH site is subject to base coupling with a DMT-protected phosphoramidite using tetrazole activator to form a phosphite triester. As a next step, any remaining unreacted 5' sites are acetylated (i.e., capped) to prevent further chain extension. This capping step can be optional, depending on the specific process being utilized. Specific inkjet processes, for example, have eliminated the need for capping/protecting and subsequent washing steps because the reactive bases are added to specific physical sites, and are thus not flushed across the entire column, chip, or plate surface as in other synthesis techniques. Subsequently, the phosphite triester is oxidized to phosphate using aqueous iodine to produce a cyanoethyl-protected phosphate backbone in preparation for the next round of extension of the DNA sequence. The DNA sequence is deprotected, and the process is repeated. When the synthesis is complete, the DNA sequence is cleaved from the support surface and deprotected. Alternately, DNA molecules can be synthesized from the 5' (attached to the solid support) to the 3' direction. Additionally, in some cases a Code_SEQ can be synthesized in its entirety, while in other cases a Code_SEQ can be synthesized in parts that are then coupled together to form the complete Code_SEQ.

Accordingly, in one specific example an encoder device can include an encoder engine configured to receive a data file having a bit sequence of binary bits encoding data. Such an encoder engine can further be configured to generate a VDNA sequence of Vnbs that reversibly encodes the bit sequence of the data file, divide the VDNA sequence into a plurality of VDNA fragments, and associate each VDNA fragment with an Arc_SEQ. The encoder engine can further be configured to generate a READ sequence of differences between each VDNA fragment and the associated Arc_SEQ that is configured to facilitate regeneration of each VDNA fragment from the associated Arc_SEQ and to generate a Code_SEQ for each VDNA fragment. The Code_SEQ can include a codename identifying the associated Arc_SEQ, the READ sequence, an Idx_SEQ including mapping of the VDNA fragment in the VDNA sequence, and a reference to the data file being encoded/decoded.

Figure 8:
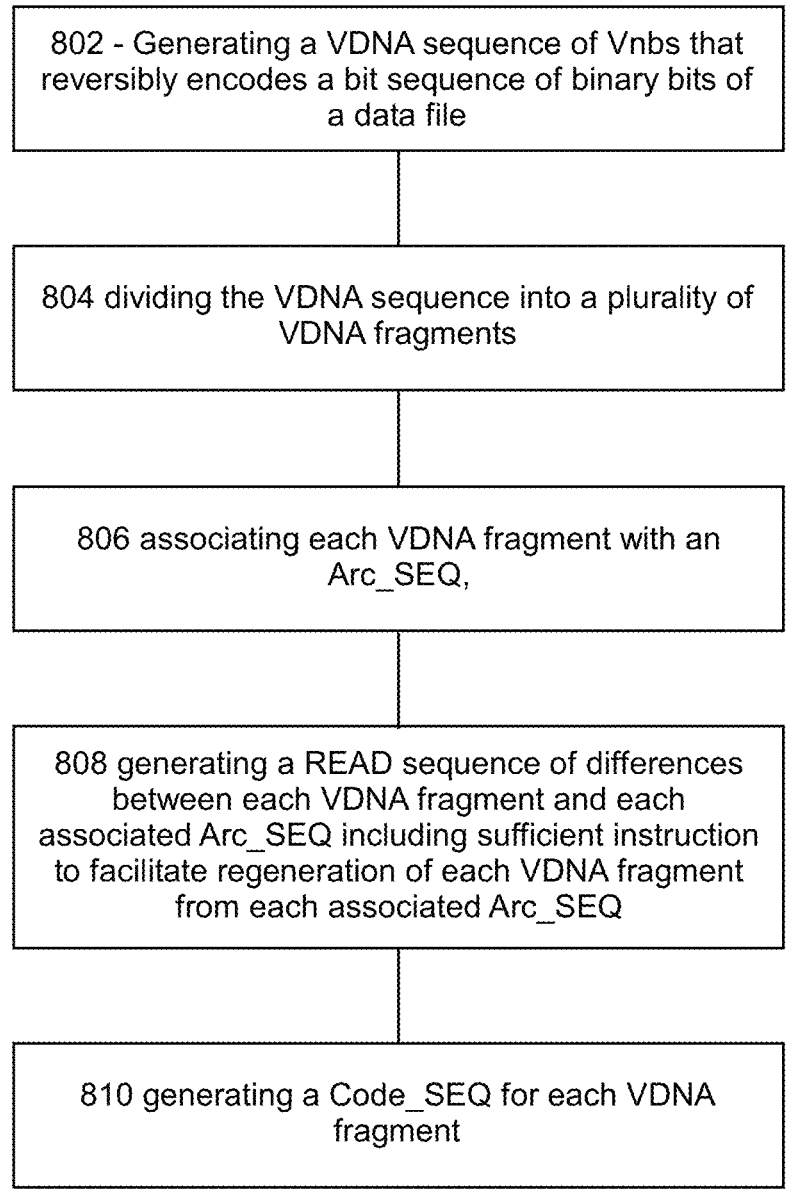
FIG. 8 shows steps performed in a method for encoding a data file in accordance with an example embodiment.

In one example, a method of encoding a data file is provided. FIG. 8 shows one example method implementation including 802 generating a VDNA sequence of Vnbs that reversibly encodes a bit sequence of binary bits of a data file, 804 dividing the VDNA sequence into a plurality of VDNA fragments, 806 associating each VDNA fragment with an Arc_SEQ, 808 generating a READ sequence of differences between each VDNA fragment and each associated Arc_SEQ including sufficient instruction to facilitate regeneration of each VDNA fragment from each associated Arc_SEQ, and 810 generating a Code_SEQ for each VDNA fragment.

Figure 9:
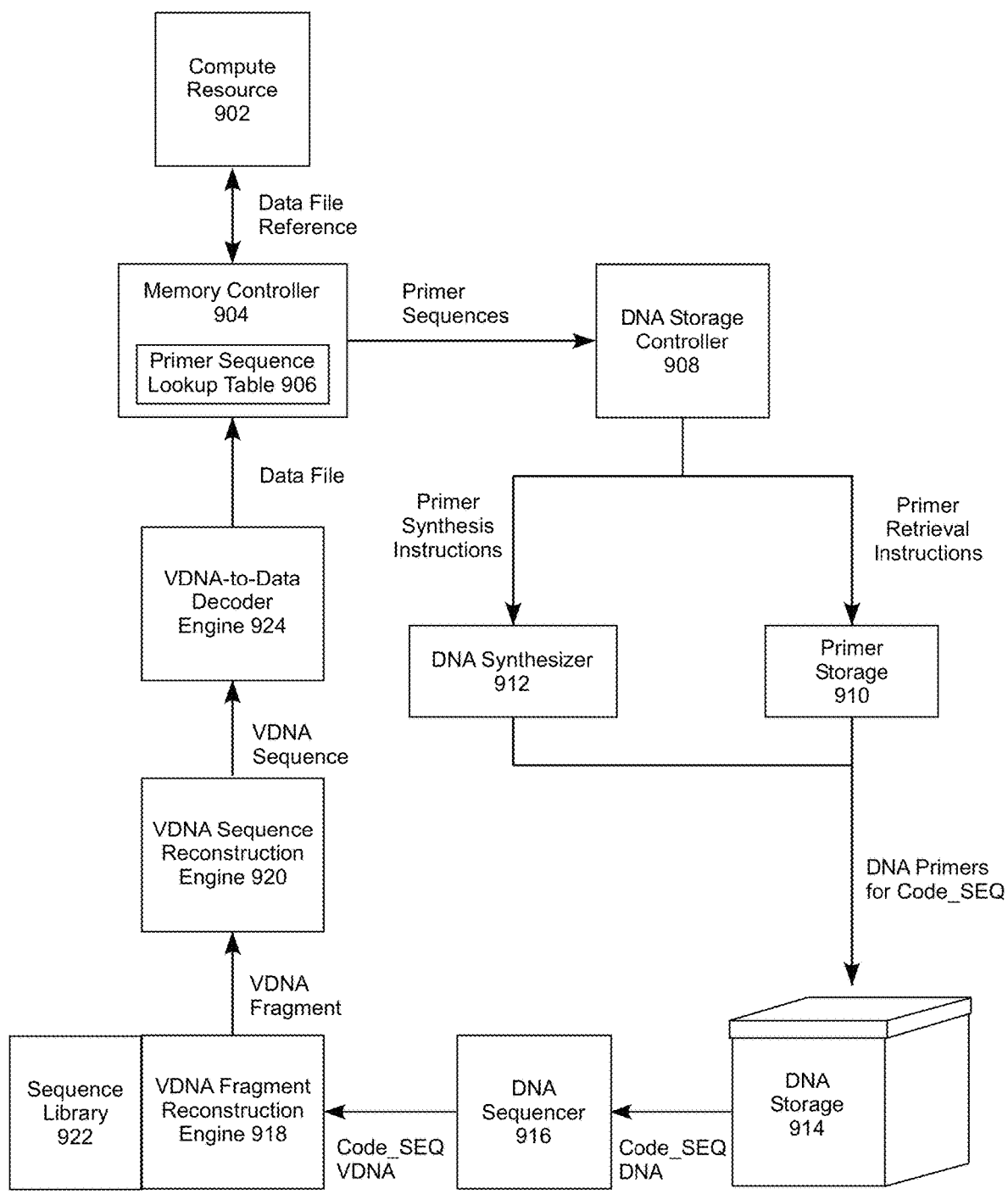
FIG. 9 shows a block diagram of a system for retrieving a data file that has been encoded and stored as DNA in accordance with an example embodiment.

FIG. 9 shows an example of retrieving a data file that has been encoded and stored as DNA. A compute resource 902 sends a read request comprising a data file reference to a memory controller 904 for retrieval of the associated data file. The memory controller 904 performs a lookup for primer sequences associated with the data file reference in a primer sequence lookup table 906, and sends the primer sequences along one of two pathways. In systems where the primer sequences are saved as physical DNA, the DNA storage controller 908 sends primer retrieval instructions to a primer storage 901, where the DNA primers for the appropriate Code_SEQs for the data file are retrieved and sent to the DNA storage 914. In systems where the primer sequences are saved as electronic or VDNA primer sequences, the DNA storage controller 908 sends primer synthesis instructions to a DNA synthesizer 912, where the DNA primers for the appropriate Code_SEQs for the data file are synthesized and sent to the DNA storage 914. The DNA primers are used to isolate and amplify the Code_SEQ DNA associated with the data file, which are sent to a DNA sequencer 916 for sequencing. Sequencing of the Code_SEQ DNA provides an electronic sequence representation of the Code_SEQ DNA, which is Code_SEQ VDNA. The Code_SEQ VDNA is sent to a VDNA fragment reconstruction engine 918, where the codename in the Code_SEQ is used to retrieve the associated Arc_SEQ from a sequence library 922. The READ of the Code_SEQ is used by the VDNA fragment reconstruction engine 918 to reconstruct the VDNA fragment from the appropriate Arc_SEQ, which is sent to the VDNA sequence reconstruction engine 920 along with the Code_SEQ. The VDNA sequence reconstruction engine 920 can then reconstruct the VDNA sequence from the Idx_SEQ indexing of each VDNA fragment associated with the data file. In other words, the VDNA sequence reconstruction engine 920 places each VDNA fragment back into its original prefragmentation order to reconstruct the VDNA sequence. This can be accomplished by regenerating the VDNA sequence directly from the VDNA fragments, or one or more VDNA segments from one or more fragmentations levels can be reconstructed, which are then in turn reassembled into the VDNA sequence. The VDNA sequence reconstruction engine can thus comprise various lookup tables, mux and logic circuits, processors, and the like, used to generate the VDNA sequence from the various VDNA segments and/or VDNA fragments.

Following reconstruction, the VDNA sequence can be sent to a VDNA-to-data decoder engine 924, which decodes the VDNA sequence into the originally encoded data file. The VDNA-to-data decoder engine 924 can vary depending on the encoding technique used to generate the VDNA sequence from the data file, which can include various lookup tables, mux and logic circuits, processors, and the like. The regenerated data file can then be sent to the memory controller 904 for filling the data request of the compute resource 902.

EXAMPLES

The following examples pertain to specific embodiments and point out specific features, elements, or steps that can be used or otherwise combined in achieving such embodiments.

In one example, there is provided an encoder device comprising an encoder engine configured to receive instructions to encode a data file having a bit sequence of binary bits encoding data, the encoder engine further configured to generate a virtual deoxyribonucleic acid (VDNA) sequence of virtual nucleotide bases (Vnb) that reversibly encodes the bit sequence of the data file, divide the VDNA sequence into a plurality of VDNA fragments, associate each VDNA fragment with an archive library sequence (Arc_SEQ), and to generate a read instruction (READ) sequence of differences between each VDNA fragment and each associated Arc_SEQ including sufficient instruction to facilitate regeneration of each VDNA fragment from each associated Arc_SEQ. The encoder device is further configured to generate a codeword sequence (Code_SEQ) for each VDNA fragment comprising a codename identifying the associated Arc_SEQ, the READ sequence associated with the VDNA fragment, and an index sequence (Idx_SEQ) including an index mapping of the VDNA fragment in the VDNA sequence.

In one example of the encoder device, to divide the VDNA sequence into the plurality of VDNA fragments, the encoder engine is further configured to divide the VDNA sequence into pluralities of successively smaller VDNA segments according to a hierarchical series of fragmentation levels to generate the plurality of VDNA fragments.

In one example of the encoder device the Idx_SEQ further comprises a series of fragmentation level indexes corresponding to the hierarchical series of fragmentation levels, each fragmentation level index including a pre-fragmentation position for each of the plurality of VDNA segments generated by that fragmentation level, wherein the plurality of VDNA fragments is generated at a final fragmentation level, and wherein the series of fragmentation level indexes provide an original position in the VDNA sequence for each of the plurality of VDNA fragments.

In one example of the encoder device the series of fragmentation level indexes include sufficient position information to reconstruct the VDNA sequence from the Idx_SEQs of the plurality of VDNA fragments.

In one example of the encoder device the READ sequence includes instructions selected from the group consisting of read direction, read start sites, read stop sites, insertion locations, deletion locations, substitution locations, sequence orientation, strand selection, and combinations thereof.

In one example of the encoder device the Code_SEQ further comprises a data file reference identifying the data file.

In one example of the encoder device the data file reference further comprises a polymerase chain reaction (PCR) primer site associating the Code_SEQ to the data file.

In one example of the encoder device the PCR primer site is specific for all of the plurality of VDNA fragments of the VDNA sequence of the data file.

In one example of the encoder device the Code_SEQ further comprises a data file reference identifying the data file, wherein the data file reference further comprises a series of polymerase chain reaction (PCR) primer sites, each PCR primer site corresponding to a fragmentation level index of the series of fragmentation level indexes.

In one example of the encoder device the encoder engine is further configured to divide the VDNA sequence into the plurality of VDNA fragments each from 100 Vnbs to 100,000 Vnbs in length.

In one example of the encoder device the encoder engine is further configured to divide the VDNA sequence into the plurality of VDNA fragments each from 500 Vnbs to 5,000 Vnbs in length.

In one example of the encoder device the Code_SEQ is a VDNA sequence.

In one example of the encoder device the Code_SEQ is a physical DNA sequence.

In one example of the encoder device each Vnb in the VDNA sequence consecutively encodes a bit-pair value of each successive pair of binary bits of the data file according to the bit sequence.

In one example of the encoder device each Vnb is one of four Vnb-types.

In one example of the encoder device the four Vnb-types include virtual adenine (VA), virtual cytosine (VC), virtual guanine (VG) and virtual thymine (VT), and wherein each of the four Vnb-types uniquely encodes for one of binary bit-pair values 00, 01, 10, or 11.

In one example of the encoder device, to generate the VDNA sequence of Vnbs, the encoder engine is further configured to partition the bit sequence of the data file into a plurality of byte-units, divide each of the plurality of byte-units into a plurality of single bit digits and a plurality of double bit digits according to a common pattern across the bit sequence, assign a specific Vnb-type to each double bit digit based on a corresponding value of each double bit digit, and assign a specific Vnb-type from a limited selection of available Vnb-types to each single bit digit based on a corresponding value of each single bit digit and limited by a Vnb-type assigned to an immediately preceding single bit digit.

In one example of the encoder device the common pattern of single bit digits and double bit digits generate a VG to VC content of about 50% and allows a homopolymer of no more than 2 of the same Vnb in the VDNA sequence.

In one example of the encoder device the encoder engine includes a member selected from the group consisting of a processor, a field-programmable gate array (FPGA), an application-specific integrated circuit (ASIC), and combinations thereof.

In one example, a data archival system is provided comprising an encoder engine configured to receive a data file having a bit sequence of binary bits encoding data, the encoder engine further configured to generate a virtual deoxyribonucleic acid (VDNA) sequence of virtual nucleotide bases (Vnb) that reversibly encodes the bit sequence of the data file, divide the VDNA sequence into a plurality of VDNA fragments, associate each VDNA fragment with an archive library sequence (Arc_SEQ), and generate a read instruction (READ) sequence of differences between each VDNA fragment and each associated Arc_SEQ including sufficient instruction to facilitate regeneration of each VDNA fragment from each associated Arc_SEQ. The encoder engine is further configured to generate a codeword sequence (Code_SEQ) for each VDNA fragment comprising a codename identifying the associated Arc_SEQ, the READ sequence associated with the VDNA fragment, and an index sequence (Idx_SEQ) including an index mapping of the VDNA fragment in the VDNA sequence. The data archival system additionally includes a deoxyribonucleic acid (DNA) synthesizer interface configured to communicatively couple to a DNA synthesizer and a DNA synthesizer controller communicatively coupled to the DNA synthesizer interface and to the encoder engine, further configured to send instructions to the DNA synthesizer to generate the Code_SEQ as a DNA sequence.

In one example of the data encoder system, to divide the VDNA sequence into the plurality of VDNA fragments, the encoder engine is further configured to divide the VDNA sequence into pluralities of successively smaller VDNA segments according to a hierarchical series of fragmentation levels to generate the plurality of VDNA fragments.

In one example of the data encoder system the idx_SEQ further comprises a series of fragmentation level indexes corresponding to the hierarchical series of fragmentation levels, each fragmentation level index including a pre-fragmentation position for each of the plurality of VDNA segments generated by that fragmentation level, wherein the plurality of VDNA fragments is generated at a final fragmentation level, and wherein the series of fragmentation level indexes provide an original position in the VDNA sequence for each of the plurality of VDNA fragments.

In one example of the data encoder system the series of fragmentation level indexes include sufficient position information to reconstruct the VDNA sequence from the Idx_SEQs of the plurality of VDNA fragments.

In one example of the data encoder system the READ sequence includes instructions selected from the group consisting of read direction, read start sites, read stop sites, insertion locations, deletion locations, substitution locations, sequence orientation, strand selection, and combinations thereof.

In one example of the data encoder system the Code_SEQ further comprises a data file reference identifying the data file.

In one example of the data encoder system the data file reference further comprises a polymerase chain reaction (PCR) primer site associating the Code_SEQ to the data file.

In one example of the data encoder system the PCR primer site is specific for all of the plurality of VDNA fragments of the VDNA sequence of the data file.

In one example of the data encoder system the Code_SEQ further comprises a data file reference identifying the data file, wherein the data file reference further comprises a series of polymerase chain reaction (PCR) primer sites, each PCR primer site corresponding to a fragmentation level index of the series of fragmentation level indexes In one example of the data encoder system the Code_SEQ is a VDNA sequence.

In one example of the data encoder system the Code_SEQ is a physical DNA sequence.

In one example of the data encoder system each Vnb in the VDNA sequence consecutively encodes a bit-pair value of each successive pair of binary bits of the data file according to the bit sequence.

In one example of the data encoder system each Vnb is one of four Vnb-types.

In one example of the data encoder system the four Vnb-types include virtual adenine (VA), virtual cytosine (VC), virtual guanine (VG) and virtual thymine (VT), and wherein each of the four Vnb-types uniquely encodes for one of binary bit-pair values 00, 01, 10, or 11.

In one example of the data encoder system, to generate the VDNA sequence of Vnbs, the encoder engine is further configured to partition the bit sequence of the data file into a plurality of byte-units, divide each of the plurality of byte-units into a plurality of single bit digits and a plurality of double bit digits according to a common pattern across the bit sequence, assign a specific Vnb-type to each double bit digit based on a corresponding value of each double bit digit, and assign a specific Vnb-type from a limited selection of available Vnb-types to each single bit digit based on a corresponding value of each single bit digit and limited by a Vnb-type assigned to an immediately preceding single bit digit.

In one example of the data encoder system the common pattern of single bit digits and double bit digits generate a VG to VC content of about 50% and allows a homopolymer of no more than 2 of the same Vnb in the VDNA sequence.

In one example of the data encoder system the encoder engine includes a member selected from the group consisting of a processor, a field-programmable gate array (FPGA), an application-specific integrated circuit (ASIC), and combinations thereof.

In one example, there is provided a method of encoding a data file comprising generating, using an encoder engine, a virtual deoxyribonucleic acid (VDNA) sequence of virtual nucleotide bases (Vnb) that reversibly encodes a bit sequence of binary bits of a data file, dividing, using the encoder engine, the VDNA sequence into a plurality of VDNA fragments, associating, using the encoder engine, each VDNA fragment with an archive library sequence (Arc_SEQ), and generating, using the encoder engine, a read instruction (READ) sequence of differences between each VDNA fragment and each associated Arc_SEQ including sufficient instruction to facilitate regeneration of each VDNA fragment from each associated Arc_SEQ. The method can additionally include generating a codeword sequence (Code_SEQ) for each VDNA fragment comprising a codename identifying the associated Arc_SEQ, the READ sequence associated with the VDNA fragment, and an index sequence (Idx_SEQ) including an index mapping of the VDNA fragment in the VDNA sequence.

In one example of the method, dividing the VDNA sequence into the plurality of VDNA fragments further comprises dividing the VDNA sequence into pluralities of successively smaller VDNA segments according to a hierarchical series of fragmentation levels to generate the plurality of VDNA fragments.

In one example of the method the Idx_SEQ further comprises a series of fragmentation level indexes corresponding to the hierarchical series of fragmentation levels, each fragmentation level index including a pre-fragmentation position for each of the plurality of VDNA segments generated by that fragmentation level, wherein the plurality of VDNA fragments is generated at a final fragmentation level, and wherein the series of fragmentation level indexes provide an original position in the VDNA sequence for each of the plurality of VDNA fragments.

In one example of the method the series of fragmentation level indexes include sufficient position information to reconstruct the VDNA sequence from the Idx_SEQs of the plurality of VDNA fragments.

In one example of the method the READ sequence includes instructions selected from the group consisting of read direction, read start sites, read stop sites, insertion locations, deletion locations, substitution locations, sequence orientation, strand selection, and combinations thereof.

In one example of the method the Code_SEQ further comprises a data file reference identifying the data file.

In one example of the method the data file reference further comprises a polymerase chain reaction (PCR) primer site.

In one example of the method the PCR primer site is specific for all of the plurality of VDNA fragments of the VDNA sequence of the data file.

In one example of the method the Code_SEQ further comprises a data file reference identifying the data file, wherein the data file reference further comprises a series of polymerase chain reaction (PCR) primer sites, each PCR primer site corresponding to a fragmentation level index of the series of fragmentation level indexes.

In one example of the method generating the Code_SEQ further comprises generating the Code_SEQ as a VDNA sequence.

In one example of the method generating the Code_SEQ further comprises generating the Code_SEQ as a physical DNA sequence.

In one example of the method generating the VDNA sequence further comprises uniquely assigning each Vnb-type to a bit-pair value and consecutively matching each successive pair of binary bits of the data file to a Vnb according to the bit-pair value.

In one example of the method herein each Vnb is one of four Vnb-types.

In one example of the method the four Vnb-types include virtual adenine (VA), virtual cytosine (VC), virtual guanine (VG) and virtual thymine (VT), and wherein each of the four Vnb-types uniquely encodes for one of binary bit-pair values 00, 01, 10, or 11.

In one example of the method, to generate the VDNA sequence of Vnbs, the method further comprises partitioning the bit sequence of the data file into a plurality of byte-units, dividing each of the plurality of byte-units into a plurality of single bit digits and a plurality of double bit digits according to a common pattern across the bit sequence, assigning a specific Vnb-type to each double bit digit based on a corresponding value of each double bit digit, and assigning a specific Vnb-type from a limited selection of available Vnb-types to each single bit digit based on a corresponding value of each single bit digit and being limited by a Vnb-type assigned to an immediately preceding single bit digit.

In one example of the method the common pattern of single bit digits and double bit digits generate a VG to VC content of about 50% and allows a homopolymer of no more than 2 of the same Vnb in the VDNA sequence.

What is claimed is:

1. An apparatus comprising:
   circuitry to:
   receive instructions to encode a data file having a bit sequence of binary bits encoding data;
   generate a virtual deoxyribonucleic acid (VDNA) sequence of virtual nucleotide bases (Vnbs) that reversibly encodes the bit sequence of the data file;
   divide the VDNA sequence into a plurality of VDNA fragments;
   associate each VDNA fragment with an archive library sequence (Arc_SEQ);
   generate a read instruction (READ) sequence of differences between each VDNA fragment and each associated Arc_SEQ including sufficient instruction to facilitate regeneration of each VDNA fragment from each associated Arc_SEQ; and
   generate a codeword sequence (Code_SEQ) for each VDNA fragment that includes:
   a codename to identify the associated Arc_SEQ;
   the READ sequence associated with the VDNA fragment; and
   an index sequence (Idx_SEQ) that includes an index mapping of the VDNA fragment in the VDNA sequence.

2. The apparatus of claim 1, wherein, to divide the VDNA sequence into the plurality of VDNA fragments, further comprises the circuitry to:
   divide the VDNA sequence into pluralities of successively smaller VDNA segments according to a hierarchical series of fragmentation levels to generate the plurality of VDNA fragments, the Idx_SEQ to also include a series of fragmentation level indexes corresponding to the hierarchical series of fragmentation levels, each fragmentation level index including a pre-fragmentation position for each of the plurality of VDNA segments, wherein the plurality of VDNA fragments is generated at a final fragmentation level, and the series of fragmentation level indexes provide an original position in the VDNA sequence for each of the plurality of VDNA fragments.

3. The apparatus of claim 2, wherein the series of fragmentation level indexes include sufficient position information to reconstruct the VDNA sequence from the Idx_SEQs of the plurality of VDNA fragments.

4. The apparatus of claim 1, wherein the READ sequence includes a read direction, read start sites, read stop sites, insertion locations, deletion locations, substitution locations, a sequence orientation, or a strand selection.

5. The apparatus of claim 1, wherein the Code_SEQ further comprises a data file reference identifying the data file.

6. The apparatus of claim 5, wherein the data file reference further comprises a polymerase chain reaction (PCR) primer site associating the Code_SEQ to the data file.

7. The apparatus of claim 6, wherein the PCR primer site is specific for all of the plurality of VDNA fragments of the VDNA sequence of the data file.

8. The apparatus of claim 1, wherein the Code_SEQ is a physical DNA sequence.

9. The apparatus of claim 1, wherein each Vnb in the VDNA sequence consecutively encodes a bit-pair value of each successive pair of binary bits of the data file according to the bit sequence.

10. The apparatus of claim 9, wherein each Vnb is one of four Vnb-types including virtual adenine (VA), virtual cytosine (VC), virtual guanine (VG) and virtual thymine (VT), and wherein each of the four Vnb-types uniquely encodes for one of binary bit-pair values 00, 01, 10, or 11.

11. The apparatus of claim 1, wherein to generate the VDNA sequence of Vnbs, further comprises the circuitry to:
partition the bit sequence of the data file into a plurality of byte-units;
divide each of the plurality of byte-units into a plurality of single bit digits and a plurality of double bit digits according to a common pattern across the bit sequence;
assign a specific Vnb-type to each double bit digit based on a corresponding value of each double bit digit; and
assign a specific Vnb-type from a limited selection of available Vnb-types to each single bit digit based on a corresponding value of each single bit digit and limited by a Vnb-type assigned to an immediately preceding single bit digit.

12. The apparatus of claim 11, wherein the common pattern of single bit digits and double bit digits generate a VG to VC content of about 50% and allows a homopolymer of no more than 2 of the same Vnb in the VDNA sequence.

13. The apparatus of claim 1, the circuitry comprising a processor, a field-programmable gate array (FPGA), or an application-specific integrated circuit (ASIC).

14. A system, comprising:
encoder circuitry to:
receive a data file having a bit sequence of binary bits encoding data;
generate a virtual deoxyribonucleic acid (VDNA) sequence of virtual nucleotide bases (Vnbs) that reversibly encodes the bit sequence of the data file;
divide the VDNA sequence into a plurality of VDNA fragments;
associate each VDNA fragment with an archive library sequence (Arc_SEQ);
generate a read instruction (READ) sequence of differences between each VDNA fragment and each associated Arc_SEQ including sufficient instruction to facilitate regeneration of each VDNA fragment from each associated Arc_SEQ; and
generate a physical DNA codeword sequence (Code_SEQ) for each VDNA fragment that includes:
a codename to identify the associated Arc_SEQ;
the READ sequence associated with the VDNA fragment; and
an index sequence (Idx_SEQ) that includes an index mapping of the VDNA fragment in the VDNA sequence;
a deoxyribonucleic acid (DNA) synthesizer interface configured to communicatively couple to a DNA synthesizer; and
a DNA synthesizer controller communicatively coupled to the DNA synthesizer interface and to the encoder circuitry, the DNA synthesizer to send instructions to the DNA synthesizer to generate the Code_SEQ as a DNA sequence.

15. The system of claim 14, wherein, to divide the VDNA sequence into the plurality of VDNA fragments, further comprises the encoder circuitry to:
divide the VDNA sequence into pluralities of successively smaller VDNA segments according to a hierarchical series of fragmentation levels to generate the plurality of VDNA fragments, the idx_SEQ to also include a series of fragmentation level indexes corresponding to the hierarchical series of fragmentation levels, each fragmentation level index including a pre-fragmentation position for each of the plurality of VDNA segments, wherein the plurality of VDNA fragments is generated at a final fragmentation level, and the series of fragmentation level indexes provide an original position in the VDNA sequence for each of the plurality of VDNA fragments.

16. The system of claim 15, wherein the series of fragmentation level indexes include sufficient position information to reconstruct the VDNA sequence from the Idx_SEQs of the plurality of VDNA fragments.

17. The system of claim 14, wherein the READ sequence includes a read direction, read start sites, read stop sites, insertion locations, deletion locations, substitution locations, a sequence orientation, or a strand selection.

18. The system of claim 14, wherein the Code_SEQ further comprises a data file reference identifying the data file, wherein the data file reference further comprises a polymerase chain reaction (PCR) primer site associating the Code_SEQ to the data file.

19. The system of claim 18, wherein the PCR primer site is specific for all of the plurality of VDNA fragments of the VDNA sequence of the data file.

20. The system of claim 14, the encoder circuitry comprising a processor, a field-programmable gate array (FPGA), or an application-specific integrated circuit (ASIC).

21. A method comprising:
generating a virtual deoxyribonucleic acid (VDNA) sequence of virtual nucleotide bases (Vnbs) that reversibly encodes a bit sequence of binary bits of a data file;
dividing the VDNA sequence into a plurality of VDNA fragments;
associating each VDNA fragment with an archive library sequence (Arc_SEQ);

generating a read instruction (READ) sequence of differences between each VDNA fragment and each associated Arc_SEQ including sufficient instruction to facilitate regeneration of each VDNA fragment from each associated Arc_SEQ; and generating a physical DNA codeword sequence (Code_SEQ) for each VDNA fragment that includes:
a codename identifying the associated Arc_SEQ;
the READ sequence associated with the VDNA fragment; and
an index sequence (Idx_SEQ) including an index mapping of the VDNA fragment in the VDNA sequence.

22. The method of claim 21, wherein dividing the VDNA sequence into the plurality of VDNA fragments further comprises dividing the VDNA sequence into pluralities of successively smaller VDNA segments according to a hierarchical series of fragmentation levels to generate the plurality of VDNA fragments, the Idx_SEQ to also include a series of fragmentation level indexes corresponding to the hierarchical series of fragmentation levels, each fragmentation level index including a pre-fragmentation position for each of the plurality of VDNA segments, wherein the plurality of VDNA fragments is generated at a final fragmentation level, and the series of fragmentation level indexes provide an original position in the VDNA sequence for each of the plurality of VDNA fragments.

23. The method of claim 21, wherein generating the VDNA sequence of Vnbs further comprises:
uniquely assigning each Vnb-type to a bit-pair value; and
consecutively matching each successive pair of binary bits of the data file to a Vnb according to the bit-pair value.

24. The method of claim 21, wherein generating the VDNA sequence of Vnbs further comprises:
partitioning the bit sequence of the data file into a plurality of byte-units;
dividing each of the plurality of byte-units into a plurality of single bit digits and a plurality of double bit digits according to a common pattern across the bit sequence;
assigning a specific Vnb-type to each double bit digit based on a corresponding value of each double bit digit; and
assigning a specific Vnb-type from a limited selection of available Vnb-types to each single bit digit based on a corresponding value of each single bit digit and being limited by a Vnb-type assigned to an immediately preceding single bit digit.

25. The method of claim 24, wherein the common pattern of single bit digits and double bit digits generate a VG to VC content of about 50% and allows a homopolymer of no more than 2 of the same Vnb in the VDNA sequence.

* * * * *

SEQUENCE LISTING

<160> NUMBER OF SEQ ID NOS: 5

<210> SEQ ID NO 1
<211> LENGTH: 24
<212> TYPE: DNA
<213> ORGANISM: Artificial Sequence
<220> FEATURE:
<223> OTHER INFORMATION: completely synthesized

```
<400> SEQUENCE: 1
aatgtaggta cataagatgc taga                                              24

<210> SEQ ID NO 2
<211> LENGTH: 21
<212> TYPE: DNA
<213> ORGANISM: Artificial Sequence
<220> FEATURE:
<223> OTHER INFORMATION: completely synthesized

<400> SEQUENCE: 2
aatgcaggta ctataagcaa t                                                 21

<210> SEQ ID NO 3
<211> LENGTH: 12
<212> TYPE: DNA
<213> ORGANISM: Artificial Sequence
<220> FEATURE:
<223> OTHER INFORMATION: completely synthesized

<400> SEQUENCE: 3
aatgcaggta ct                                                           12

<210> SEQ ID NO 4
<211> LENGTH: 12
<212> TYPE: DNA
<213> ORGANISM: Artificial Sequence
<220> FEATURE:
<223> OTHER INFORMATION: completely synthesized

<400> SEQUENCE: 4
agacacatgt tg                                                           12

<210> SEQ ID NO 5
<211> LENGTH: 90
<212> TYPE: DNA
<213> ORGANISM: Artificial Sequence
<220> FEATURE:
<223> OTHER INFORMATION: completely synthesized

<400> SEQUENCE: 5
agacacatgt tgatcagagt gagtgtgtga gcagagagac gagtgaacat gacagtcact        60
gcagagagag ctagacgtgg acacagtgga                                        90
```